US012312596B2

(12) United States Patent
Ryu et al.

(10) Patent No.: US 12,312,596 B2
(45) Date of Patent: May 27, 2025

(54) METHOD OF TRANSDIFFERENTIATING HAIR FOLLICLE STEM CELLS INTO SPERM STEM CELLS

(71) Applicant: CHUNG-ANG UNIVERSITY INDUSTRY-ACADEMIC COOPERATION FOUNDATION, Seoul (KR)

(72) Inventors: Buom-Yong Ryu, Gyeonggi-do (KR); Yong-Hee Kim, Seoul (KR)

(73) Assignee: CHUNG-ANG UNIVERSITY INDUSTRY-ACADEMIC COOPERATION FOUNDATION, Seoul (KR)

( * ) Notice: Subject to any disclaimer, the term of this patent is extended or adjusted under 35 U.S.C. 154(b) by 379 days.

(21) Appl. No.: 16/476,891

(22) PCT Filed: Jan. 9, 2018

(86) PCT No.: PCT/KR2018/000434
§ 371 (c)(1),
(2) Date: Jul. 10, 2019

(87) PCT Pub. No.: WO2018/131872
PCT Pub. Date: Jul. 19, 2018

(65) Prior Publication Data
US 2020/0157496 A1    May 21, 2020

(30) Foreign Application Priority Data

Jan. 10, 2017  (KR) .................. 10-2017-0003310

(51) Int. Cl.
*C12N 5/00*    (2006.01)
*C12N 5/071*   (2010.01)
*C12N 5/0735*  (2010.01)
*C12N 5/076*   (2010.01)
*C12N 5/0775*  (2010.01)

(52) U.S. Cl.
CPC .......... *C12N 5/0611* (2013.01); *C12N 5/0037* (2013.01); *C12N 5/0608* (2013.01); *C12N 5/061* (2013.01); *C12N 5/0628* (2013.01); *C12N 5/0666* (2013.01); *C12N 2500/90* (2013.01); *C12N 2501/115* (2013.01); *C12N 2501/13* (2013.01); *C12N 2506/092* (2013.01)

(58) Field of Classification Search
USPC .......................................................... 435/325
See application file for complete search history.

(56) References Cited

U.S. PATENT DOCUMENTS

2007/0192881 A1* 8/2007 Brinster ............. G01N 33/5073
800/14
2007/0202590 A1    8/2007 Shinohara et al.

FOREIGN PATENT DOCUMENTS

CN    103146644    *    6/2013
CN    103146644 A         6/2013

OTHER PUBLICATIONS

Higaki (Scientific Reports, 2017, vol. 7, 42852, p. 1-14).*
Easley (Cell Reports, 2012, vol. 2, p. 440-446).*
Rombaut (Mol. Human Reprod., 2018, vol. 24, No. 2, p. 47-54).*
Wei (Scientific Reports, 2016, vol. 6, No. 36779, p. 1-9).*
Ge (Scientific Reports, 2015, vol. 5, No. 13822, p. 1-9).*
Martin (BioMed International, 2013, vol. 2013, Article 384734, p. 1-9).*
Mazaheri (Avicenna J. Med. Biotech., 2012, vol. 4, No. 2, p. 55-63).*
Shi (Animal Reprod. Sci., 2014, vol. 147, No. 1-2, p. 74-85).*
Nikolic, Stem Cells International, 2016, Article ID 1741072, p. 1-8.*
Zhou (Nature cell Biol., 2009, vol. 11, No. 5, p. 631-636, plus supplementary information.*
Amidi, In Vitro Cell Dev. Biol.—Animal, 2015, vol. 51, p. 1093-1101.*
Dyce (PLoS One, May 2011, vol. 6, No. 5, e20339, p. 1-14).*
Ge et al., "Differentiation of early germ cells from human skin-derived stem cells without exogenous gene integration," Scientific Reports, Sep. 8, 2015, vol. 5(13822), pp. 1-9.
Martin et al., "Propagation of Adult SSCs: From Mouse to Human," BioMed Research International, 2013, vol. 2013 (384734), pp. 1-9.
Ryu et al., "Conservation of spermatogonial stem cell self-renewal signaling between mouse and rat," PNAS, Oct. 4, 2005, vol. 102(40), pp. 14302-14307.

* cited by examiner

*Primary Examiner* — Michael C Wilson
(74) *Attorney, Agent, or Firm* — Riverside Law LLP

(57) ABSTRACT

The present invention relates to a method for differentiating hair follicle cells into germline stem cells, germline stem cells differentiated by the method, and use of the same germline stem cells. A method of differentiating hair follicle cells into germline stem cells according to the present invention can differentiate hair follicle cells into germline stem cells using culture conditions only, without genetic modification. Capable of inducing differentiation of cells of specific individual types, such as hair follicle cells, into cells of different types such as germline cells, the present invention is therefore expected to be usefully used for the understanding of reproductive biology and the clinical application thereof.

5 Claims, 25 Drawing Sheets

Specification includes a Sequence Listing.

SEQUENCE LISTING

<160> NUMBER OF SEQ ID NOS: 42

<210> SEQ ID NO 1
<211> LENGTH: 25
<212> TYPE: DNA
<213> ORGANISM: Artificial Sequence
<220> FEATURE:
<223> OTHER INFORMATION: H19 Outer Forward Primer (5' - 3')

<400> SEQUENCE: 1
taaggagatt atgtttattt ttgga          25

<210> SEQ ID NO 2
<211> LENGTH: 24
<212> TYPE: DNA
<213> ORGANISM: Artificial Sequence
<220> FEATURE:
<223> OTHER INFORMATION: H19 Outer Reverse Primer (5' - 3')

<400> SEQUENCE: 2 cccccctaata acatttataa cccc                                          24

<210> SEQ ID NO 3
<211> LENGTH: 24
<212> TYPE: DNA
<213> ORGANISM: Artificial Sequence
<220> FEATURE:
<223> OTHER INFORMATION: H19 Inner Forward Primer (5' - 3')

<400> SEQUENCE: 3
aaggagatta tgtttatttt tgga                                           24

<210> SEQ ID NO 4
<211> LENGTH: 26
<212> TYPE: DNA
<213> ORGANISM: Artificial Sequence
<220> FEATURE:
<223> OTHER INFORMATION: H19 Inner Reverse Primer (5' - 3')

<400> SEQUENCE: 4
aaacttaaat aacccacaac attacc                                         26

<210> SEQ ID NO 5
<211> LENGTH: 30
<212> TYPE: DNA
<213> ORGANISM: Artificial Sequence
<220> FEATURE:
<223> OTHER INFORMATION: Igf2 Outer Forward Primer (5' - 3')

<400> SEQUENCE: 5
ggttaggtga aggttttgtg ggtagttata                                     30

<210> SEQ ID NO 6
<211> LENGTH: 30
<212> TYPE: DNA
<213> ORGANISM: Artificial Sequence
<220> FEATURE:
<223> OTHER INFORMATION: Igf2 Outer Reverse Primer (5' - 3')

<400> SEQUENCE: 6
atattcccct ttcaaattcc aatctacatc                                     30

<210> SEQ ID NO 7
<211> LENGTH: 30
<212> TYPE: DNA
<213> ORGANISM: Artificial Sequence
<220> FEATURE:
<223> OTHER INFORMATION: Igf2 Inner Forward Primer (5' - 3')

<400> SEQUENCE: 7
ggtggttttt taatggatat tttaaggtga                                     30

<210> SEQ ID NO 8
<211> LENGTH: 30
<212> TYPE: DNA
<213> ORGANISM: Artificial Sequence
<220> FEATURE:

```
<223> OTHER INFORMATION: Igf2 Inner Reverse Primer (5' - 3')

<400> SEQUENCE: 8
ccaacctcta tccctaactt ttctaacctc                                    30

<210> SEQ ID NO 9
<211> LENGTH: 26
<212> TYPE: DNA
<213> ORGANISM: Artificial Sequence
<220> FEATURE:
<223> OTHER INFORMATION: Peg1 Outer Forward Primer (5' - 3')

<400> SEQUENCE: 9
aatttggggt ttaggattag agattt                                        26

<210> SEQ ID NO 10
<211> LENGTH: 25
<212> TYPE: DNA
<213> ORGANISM: Artificial Sequence
<220> FEATURE:
<223> OTHER INFORMATION: Peg1 Outer Reverse Primer (5' - 3')

<400> SEQUENCE: 10
acaacaaaaa caacaaacaa caact                                         25

<210> SEQ ID NO 11
<211> LENGTH: 27
<212> TYPE: DNA
<213> ORGANISM: Artificial Sequence
<220> FEATURE:
<223> OTHER INFORMATION: Peg1 Inner Forward Primer (5' - 3')

<400> SEQUENCE: 11
agagatttat aaggaaagag ggggtag                                       27

<210> SEQ ID NO 12
<211> LENGTH: 25
<212> TYPE: DNA
<213> ORGANISM: Artificial Sequence
<220> FEATURE:
<223> OTHER INFORMATION: Peg1 Inner Reverse Primer (5' - 3')

<400> SEQUENCE: 12
acaacaaaaa caacaaacaa caact                                         25

<210> SEQ ID NO 13
<211> LENGTH: 25
<212> TYPE: DNA
<213> ORGANISM: Artificial Sequence
<220> FEATURE:
<223> OTHER INFORMATION: Peg3 Outer Forward Primer (5' - 3')

<400> SEQUENCE: 13
ttttgtagag gattttgata aggag                                         25

<210> SEQ ID NO 14
<211> LENGTH: 25
<212> TYPE: DNA
<213> ORGANISM: Artificial Sequence
<220> FEATURE:
<223> OTHER INFORMATION: Peg3 Outer Reverse Primer (5' - 3')

<400> SEQUENCE: 14
catactacaa aacaaccaaa taacc                                         25
```

```
<210> SEQ ID NO 15
<211> LENGTH: 25
<212> TYPE: DNA
<213> ORGANISM: Artificial Sequence
<220> FEATURE:
<223> OTHER INFORMATION: Peg3 Inner Forward Primer (5' - 3')

<400> SEQUENCE: 15
tgtagaggat tttgataagg aggtg                                        25

<210> SEQ ID NO 16
<211> LENGTH: 25
<212> TYPE: DNA
<213> ORGANISM: Artificial Sequence
<220> FEATURE:
<223> OTHER INFORMATION: Peg3 Inner Reverse Primer (5' - 3')

<400> SEQUENCE: 16
caatctaata cacccacact aaacc                                        25

<210> SEQ ID NO 17
<211> LENGTH: 20
<212> TYPE: DNA
<213> ORGANISM: Artificial Sequence
<220> FEATURE:
<223> OTHER INFORMATION: Bcl6b Forward Primer (5' - 3')

<400> SEQUENCE: 17
cattttcggc acaagagtca                                              20

<210> SEQ ID NO 18
<211> LENGTH: 20
<212> TYPE: DNA
<213> ORGANISM: Artificial Sequence
<220> FEATURE:
<223> OTHER INFORMATION: Bcl6b Reverse Primer (5' - 3')

<400> SEQUENCE: 18
ttagatggtg gggactcagc                                              20

<210> SEQ ID NO 19
<211> LENGTH: 22
<212> TYPE: DNA
<213> ORGANISM: Artificial Sequence
<220> FEATURE:
<223> OTHER INFORMATION: Dnd1 Forward Primer (5' - 3')

<400> SEQUENCE: 19
ccctaaatgg gttaagcaga gc                                           22

<210> SEQ ID NO 20
<211> LENGTH: 23
<212> TYPE: DNA
<213> ORGANISM: Artificial Sequence
<220> FEATURE:
<223> OTHER INFORMATION: Dnd1 Reverse Primer (5' - 3')

<400> SEQUENCE: 20
ggcaaggttc ctcacaacta aag                                          23

<210> SEQ ID NO 21
<211> LENGTH: 20
<212> TYPE: DNA
<213> ORGANISM: Artificial Sequence
<220> FEATURE:
<223> OTHER INFORMATION: Egr3 Forward Primer (5' - 3')
```

-continued

<400> SEQUENCE: 21
tttgcctgtg agttctgtgg								20

<210> SEQ ID NO 22
<211> LENGTH: 20
<212> TYPE: DNA
<213> ORGANISM: Artificial Sequence
<220> FEATURE:
<223> OTHER INFORMATION: Egr3 Reverse Primer (5' - 3')

<400> SEQUENCE: 22
cccctttctc cgacttcttc								20

<210> SEQ ID NO 23
<211> LENGTH: 20
<212> TYPE: DNA
<213> ORGANISM: Artificial Sequence
<220> FEATURE:
<223> OTHER INFORMATION: Fos Forward Primer (5' - 3')

<400> SEQUENCE: 23
tacactccaa gcggagacag								20

<210> SEQ ID NO 24
<211> LENGTH: 20
<212> TYPE: DNA
<213> ORGANISM: Artificial Sequence
<220> FEATURE:
<223> OTHER INFORMATION: Fos Reverse Primer (5' - 3')

<400> SEQUENCE: 24
tccttctcct tcagcaggtt								20

<210> SEQ ID NO 25
<211> LENGTH: 20
<212> TYPE: DNA
<213> ORGANISM: Artificial Sequence
<220> FEATURE:
<223> OTHER INFORMATION: Id4 Forward Primer (5' - 3')

<400> SEQUENCE: 25
gctcgtgcct accatcccgc								20

<210> SEQ ID NO 26
<211> LENGTH: 21
<212> TYPE: DNA
<213> ORGANISM: Artificial Sequence
<220> FEATURE:
<223> OTHER INFORMATION: Id4 Reverse Primer (5' - 3')

<400> SEQUENCE: 26
ggtggcggct gtctcagcaa a								21

<210> SEQ ID NO 27
<211> LENGTH: 24
<212> TYPE: DNA
<213> ORGANISM: Artificial Sequence
<220> FEATURE:
<223> OTHER INFORMATION: Nanos3 Forward Primer (5' - 3')

<400> SEQUENCE: 27
caagccaagt tcagaaagcc agca							24

<210> SEQ ID NO 28
<211> LENGTH: 24

```
<212> TYPE: DNA
<213> ORGANISM: Artificial Sequence
<220> FEATURE:
<223> OTHER INFORMATION: Nanos3 Reverse Primer (5' - 3')

<400> SEQUENCE: 28
aggacatggg actgatagat ggca                                          24

<210> SEQ ID NO 29
<211> LENGTH: 19
<212> TYPE: DNA
<213> ORGANISM: Artificial Sequence
<220> FEATURE:
<223> OTHER INFORMATION: Ret Forward Primer (5' - 3')

<400> SEQUENCE: 29
tcccttccac atggattga                                                19

<210> SEQ ID NO 30
<211> LENGTH: 20
<212> TYPE: DNA
<213> ORGANISM: Artificial Sequence
<220> FEATURE:
<223> OTHER INFORMATION: Ret Reverse Primer (5' - 3')

<400> SEQUENCE: 30
atcggctctc gtgagtggta                                               20

<210> SEQ ID NO 31
<211> LENGTH: 21
<212> TYPE: DNA
<213> ORGANISM: Artificial Sequence
<220> FEATURE:
<223> OTHER INFORMATION: Sall4 Forward Primer (5' - 3')

<400> SEQUENCE: 31
agcactgctg cacacggtgt g                                             21

<210> SEQ ID NO 32
<211> LENGTH: 21
<212> TYPE: DNA
<213> ORGANISM: Artificial Sequence
<220> FEATURE:
<223> OTHER INFORMATION: Sall4 Reverse Primer (5' - 3')

<400> SEQUENCE: 32
gtcatgtagt gtaccttcag g                                             21

<210> SEQ ID NO 33
<211> LENGTH: 24
<212> TYPE: DNA
<213> ORGANISM: Artificial Sequence
<220> FEATURE:
<223> OTHER INFORMATION: Thy1 Forward Primer (5' - 3')

<400> SEQUENCE: 33
tggactgccg ccatgagaat aaca                                          24

<210> SEQ ID NO 34
<211> LENGTH: 24
<212> TYPE: DNA
<213> ORGANISM: Artificial Sequence
<220> FEATURE:
<223> OTHER INFORMATION: Thy1 Reverse Primer (5' - 3')

<400> SEQUENCE: 34
```
tggtggtgaa gttggctagg gtaa                                          24

<210> SEQ ID NO 35
<211> LENGTH: 20
<212> TYPE: DNA
<213> ORGANISM: Artificial Sequence
<220> FEATURE:
<223> OTHER INFORMATION: Dazl Forward Primer (5' - 3')

<400> SEQUENCE: 35
tccttgactt gtggttgctg                                               20

<210> SEQ ID NO 36
<211> LENGTH: 20
<212> TYPE: DNA
<213> ORGANISM: Artificial Sequence
<220> FEATURE:
<223> OTHER INFORMATION: Dazl Reverse Primer (5' - 3')

<400> SEQUENCE: 36
ccaccttcga ggttttacca                                               20

<210> SEQ ID NO 37
<211> LENGTH: 22
<212> TYPE: DNA
<213> ORGANISM: Artificial Sequence
<220> FEATURE:
<223> OTHER INFORMATION: Gapdh Forward Primer (5' - 3')

<400> SEQUENCE: 37
ctgacgtgcc gcctggagaa ac                                            22

<210> SEQ ID NO 38
<211> LENGTH: 24
<212> TYPE: DNA
<213> ORGANISM: Artificial Sequence
<220> FEATURE:
<223> OTHER INFORMATION: Gapdh Reverse Primer (5' - 3')

<400> SEQUENCE: 38
ccccggcatc gaaggtggaa gagt                                          24

<210> SEQ ID NO 39
<211> LENGTH: 21
<212> TYPE: DNA
<213> ORGANISM: Artificial Sequence
<220> FEATURE:
<223> OTHER INFORMATION: Gfp Forward Primer (5' - 3')

<400> SEQUENCE: 39
gcaagctgac cctgaagttc a                                             21

<210> SEQ ID NO 40
<211> LENGTH: 21
<212> TYPE: DNA
<213> ORGANISM: Artificial Sequence
<220> FEATURE:
<223> OTHER INFORMATION: Gfp Reverse Primer (5' - 3')

<400> SEQUENCE: 40
tcaccttgat gccgttcttc t                                             21

<210> SEQ ID NO 41
<211> LENGTH: 20
<212> TYPE: DNA
<213> ORGANISM: Artificial Sequence

```
<220> FEATURE:
<223> OTHER INFORMATION: Actb Forward Primer (5' - 3')

<400> SEQUENCE: 41
cgccatggat gacgatatcg                                              20

<210> SEQ ID NO 42
<211> LENGTH: 20
<212> TYPE: DNA
<213> ORGANISM: Artificial Sequence
<220> FEATURE:
<223> OTHER INFORMATION: Actb Reverse Primer (5' - 3)

<400> SEQUENCE: 42
cgaagccggc tttgcacatg                                              20
```

METHOD OF TRANSDIFFERENTIATING HAIR FOLLICLE STEM CELLS INTO SPERM STEM CELLS

STATEMENT REGARDING GOVERNMENT RIGHTS

The present invention was undertaken with the support of Bio and Medical Technology Development Program of the National Research Foundation of Korea (NRF) No. 2018M3A9H1023139 grant funded by the Ministry of Science and ICT, Republic of Korea.

CROSS-REFERENCE TO RELATED APPLICATIONS

This application is the U.S. national phase application filed under 35 U.S.C. § 371 claiming benefit to International Patent Application No. PCT/KR2018/000434, filed on Jan. 9, 2018, which is entitled to priority under to Korean Patent Application No. 10-2017-0003310, filed Jan. 10, 2017.

TECHNICAL FIELD

The present invention relates to a method for differentiating hair follicle cells into germline stem cells, germline stem cells differentiated by the method, and use of the same germline stem cells.

BACKGROUND ART

Spermatogenesis is the process during which male gametes or spermatozoa mature, and spermatozoa are produced throughout the entire male lifetime. Spermatogenesis depends on spermatogonial stem cells (SSCs), which are adult stem cells capable of both self-renewal and differentiation. The SSCs rarely appear in the testicles of rodents, and are estimated to be 2 to 3 cells per 10,000 cells in an adult mouse and approximately 2 cells per 1,000 cells in an adult rat. Although the importance of SSCs in male reproduction is recognized, it is difficult to study the SSC biology in detail due to the rarity of SSCs in general animal models as described above. Accordingly, purification and in vitro culture methods of SSCs have been studied in various species. Further, the stem cell function of SSCs may be evaluated based on their ability to undergo the process of spermatogenesis through direct spermatogonial transplantation into the testicles of an infertile individual.

In previous studies, many researchers have reported that germ cell-like cells may be derived from pluripotent stem cell lines. Oocytes were successfully derived from mouse embryonic stem cells (ESCs), and male germ cells generated from ESCs and ES-derived germ cells are subjected to the process of spermatogenesis to produce mature spermatozoa (sperm), and the sperms were subjected to spermatogonial transplantation in the testicles of adult mice. Male germ cells capable of producing offspring from the mouse ESCs were successfully produced.

Furthermore, recent studies have reported that induced pluripotent stem cells (iPSCs) and pluripotent cell lines may be differentiated into germ cells in vitro, and particularly, mouse iPSCs were able to be differentiated into presumptive germ cells in the round iPSC-induced form resembling immature ova and embryonic bodies. Further, through epiblast-like cells, culture conditions required to reconstitute a specific PGC pathway for generating primordial germ cell-like cells from ESCs and iPSCs in mice were confirmed, and the primordial germ cell-like cells produced normal imprinting pattern offspring through the spermatogenesis process after transplantation.

A hair follicle (HF) is a characterized niche for adult stem cells, and contains epithelial and melanocytic stem cells. Hair follicle cells may be an accessible source of interfollicular epidermis, hair follicle structure, and sebaceous gland, as well as pluripotent adult stem cells that reconstitute-generate new hair in vivo. These unique hair follicle stem/progenitor cells are located at the insertion point of the arrector pili muscle below the entrance of the sebaceous gland of the outer root sheath called the bulge region of the hair follicle. In previous studies, the hair follicle stem cell population was named retaining cells characterized by its ability to maintain DNA labels for a long period of time. In addition, these cells were reported to express nestin, cytokeratin 15, cytokeratin 19, and CD34. Recently, it has been reported that HF stem cells in the bulge and sub-bulge regions of the outer root sheath contribute to the melanocytic lineage of adult mice, and the nestin expression was found in hair follicle cells above/below the bulge region below the sebaceous gland.

It has been reported that these nestin-positive hair follicle cells may give rise to neurons, smooth muscle cells, glial cells, keratinocytes, and other cell types, and neural crest stem cells and skin epidermis-derived progenitors may be differentiated into various cell types including neurons, smooth muscle cells, glial cells, keratinocytes, and melanin cells.

Other studies similarly have reported that multipotent adult stem cells isolated and cultured from human and mouse hair follicles exhibit pluripotency. However, it is not known whether these hair follicle cells may be transdifferentiated into germ cells, and it is very important to study such transdifferentiation in stem cell biology.

DISCLOSURE

Technical Problem

To solve the problems in the related art as described above, as a result of assuming that hair follicle cells may be transdifferentiated into germline cells under conditions similar to those used for culturing spermatogonial stem cells (SSCs) and conducting intensive studies on the potential stability of SSC culture conditions of these hair follicle cells, the present inventors established a method of producing germline cells including stem cells from mouse hair follicle cells and obtained hair follicle-derived germline cells by the method, thereby completing the present invention.

Thus, an object of the present invention is to provide a method for differentiating hair follicle cells into germline stem cells, the method including: a step of culturing hair follicle cells on feeder cells using a spermatogonial stem cell differentiation medium containing a growth factor.

Further, another object of the present invention is to provide germline stem cells differentiated by the differentiation method.

However, technical problems to be achieved by the present invention are not limited to the aforementioned problems, and other problems that are not mentioned may be clearly understood by those skilled in the art from the following description.

Technical Solution

In order to achieve the objects of the present invention as described above, the present invention provides a method for differentiating hair follicle cells into germline stem cells, the method including: a step of culturing hair follicle cells on feeder cells using a spermatogonial stem cell differentiation medium containing a growth factor.

Further, the present invention provides germline stem cells differentiated by the differentiation method.

Advantageous Effects

The present invention relates to a method for differentiating hair follicle cells into germline stem cells, germline stem cells differentiated by the method, and use of the same germline stem cells. A method of differentiating hair follicle cells into germline stem cells according to the present invention can differentiate hair follicle cells into germline stem cells using culture conditions only, without genetic modification. Since it is possible to induce differentiation of cells of specific individual types, such as hair follicle cells, into cells of different types such as germline cells, the present invention is expected to be usefully used for the understanding of reproductive biology and the clinical application thereof.

MODES OF THE INVENTION

Figure 1:
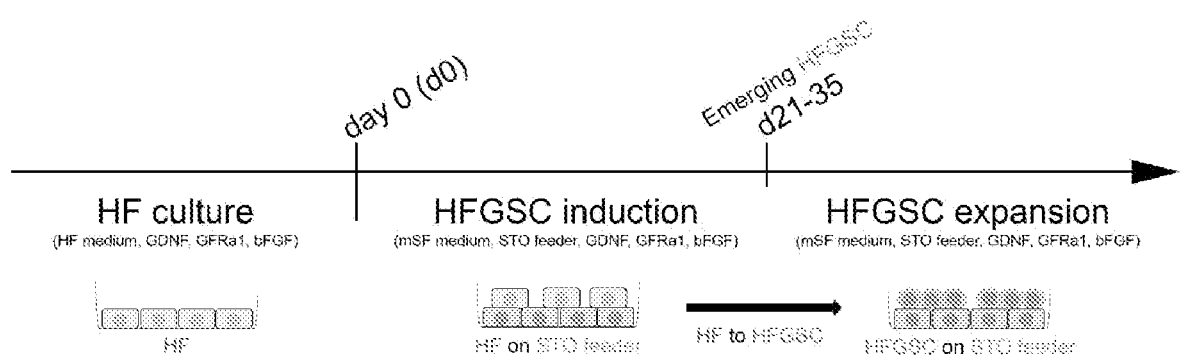
FIG. 1 is a view schematically illustrating the GSC-like culture conditions of the present invention.
Figure 1:
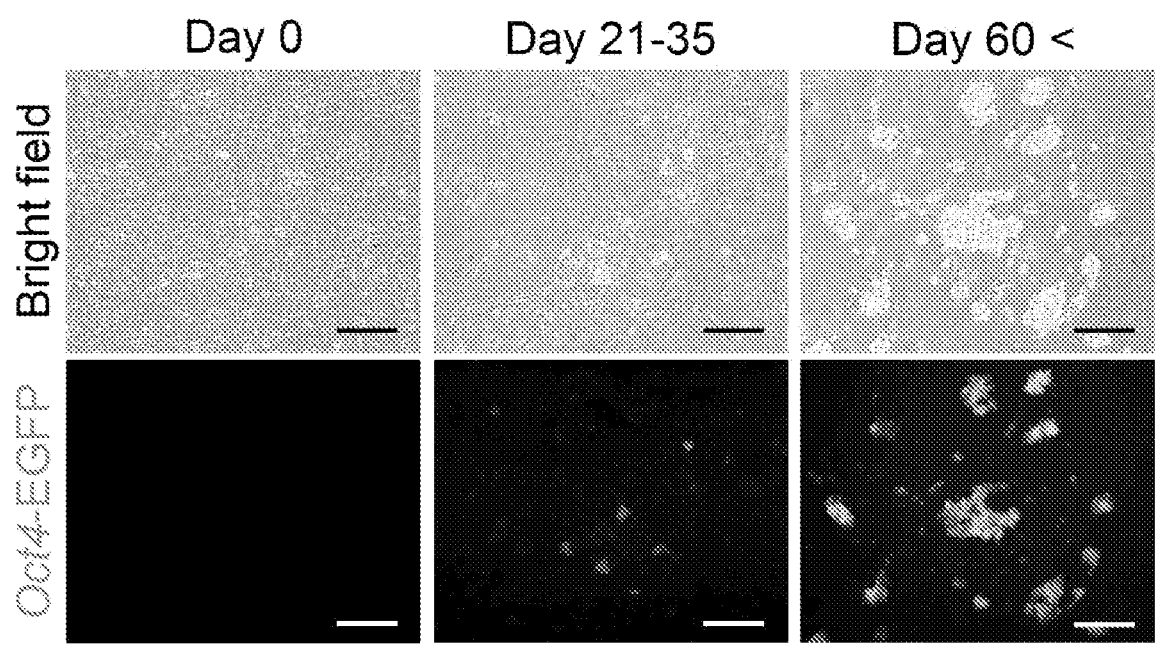

The present invention relates to a method for differentiating hair follicle cells into germline stem cells, germline stem cells differentiated by the method, and use of the same germline stem cells.

As a result of intensive studies on a method capable of differentiating hair follicle cells into germline stem cells, the present inventors established a differentiation method capable of differentiating hair follicle cells into germline stem cells without genetic modification and obtained germline stem cells by culturing hair follicle cells by the method, thereby completing the present invention based on this.

Thus, the present invention provides a method for differentiating hair follicle cells into germline stem cells, the method including: a step of culturing hair follicle cells on feeder cells using a spermatogonial stem cell differentiation medium containing a growth factor.

In the present invention, the growth factor may be a glial cell line-derived neurotrophic factor (GDNF), GDNF family receptor α1 (GFRα1), and a basic fibroblast growth factor (bFGF), but is not limited thereto.

The spermatogonial stem cell differentiation medium may be a mouse serum-free medium (mSFM), and may include a culture medium additive which may be typically used in the art.

As used herein, the "feeder cells" are known to secrete trophic factors which contribute to maintaining the undifferentiated state of embryonic stem cells and known to be associated with an undifferentiated maintenance mechanism mediated by cell contact. Signaling substances secreted from feeder cells contribute to regulating the undifferentiation maintenance or initiation of differentiation of embryonic stem cells. Examples of the substances secreted from feeder cells include a wingless-type MMTV integration site family (Wnt), bone morphogenetic proteins (BMPs), a transforming growth factor-beta (TGF-β), an extracellular matrix, and the like. There have been reports of differentiation into embryonic stem cells or induced pluripotent stem cells using various mouse or human-derived feeder cells. In the present invention, as the feeder cell, STO cells may be used, but the feeder cell is not limited thereto.

In the present invention, hair follicle cells may be cultured under the culture conditions for 3 to 5 weeks, and thus may be induced to be differentiated into germline stem cells.

As used herein, the term "germline stem cells" is a type of adult stem cells, and includes spermatogonial stem cells (SSCs) or oocyte precursor stem cells, and particularly, spermatogonial stem cells refer to cells having the unipotency capable of producing sperm through self-proliferation and differentiation. Germline stem cells are very few in number, are present at rest in a safe place between feeder cells in the testicles, and are characterized in that proliferation and differentiation are regulated by interaction with external signals including feeder cells.

In the Examples of the present invention, it was confirmed that hair follicle cells are cultured by the differentiation method and are differentiated into germline stem cell-like cells expressing germline stem cell-like morphologies, sizes, and spermatogonia specific genes.

In some Examples of the present invention, in order to establish differentiation conditions capable of specifically differentiating hair follicle cells into germline stem cells, a culture medium, a growth factor, and a type of feeder cells capable of effectively improving the differentiation ability were determined, and an optimal differentiation method was established through the determination (see Examples 2 to 4).

In the other Examples of the present invention, through the fact that after hair follicle cells were cultured by the differentiation method according to the present invention, the expression level of various spermatogonia specific genes was increased and the expression of genes specific for other lineage cells, that is, hair follicle cells was not increased, it was confirmed that hair follicle cells were differentiated into germline stem cells. Further, through the observation by a microscope, it was confirmed that the differentiated cells exhibited a morphology similar to spermatogonial stem cells (see Examples 5 to 8).

From the foregoing, the differentiation method according to the present invention is expected to be capable of being very usefully used for differentiating hair follicle cells into germline stem cells.

Thus, the present invention provides germline stem cells differentiated by the differentiation method.

Hereinafter, preferred Examples for helping the understanding of the present invention will be suggested. However, the following Examples are provided only to more easily understand the present invention, and the contents of the present invention are not limited by the following Examples.

EXAMPLES

Example 1. Experimental Preparation and Experimental Method 1-1. Experimental Animal B6CBA-Tg(Pou5f1-EGFP) 2Mnn (OG2) used in the experiment were purchased from Harlan Laboratories (Indianapolis, IN, USA). WBB6F1-W/W$^v$ mice were purchased from Jackson Laboratory (Bar Harbor, Me, USA), and were used as recipients in the SSC quantification experiment. B6D2F1 (C57BL/6J×DBA/2J F1 hybrid; Koatech) mice were used as oocyte donors in a sperm direct injection method (intracytoplasmic sperm injection, ICSI). The mice were provided with a standard diet ad libitum, and bred under conditions of 21±2° C., 55±10% humidity, and a day/night cycle condition of 12 hours (lights on at 7 am and off at 7 pm). The animal experiments of the present invention were approved by the Laboratory Animal Care and Use Committee of Chung-Ang University, and were performed according to the Laboratory Animal Care and Use Manual issued by the National Institutes of Health.

1-2. Isolation and Collection of Hair Follicle Cells

Hair follicle (HF) cells were collected from OG2 mice expressing an enhanced green fluorescent protein (EGFP) under the control of the POU domain, the class 5, the transcription factor 1, a promoter, and a distal enhancer. The isolation and culture of hair follicle cells were performed with minor modifications to a previously disclosed protocol (Nath, M., Offers, M., Hummel, M. & Seissler, J. Isolation and in vitro expansion of Lgr6-positive multipotent hair follicle stem cells. Cell and tissue research 344, 435-444, doi:10.1007/s00441-011-1165-y (2011).).

More specifically, after the dorsal skin was epilated by plucking, a piece of the dorsal skin (1×2 cm) was collected, treated with 2.5 mg/ml of dispase diluted with Dulbecco's Modified Eagle Medium/Nutrient Mixture F-12 (DMEM/F12, 1:1 mixture; Thermo Fisher Scientific, Waltham, MA, USA), and cultured at 4° C. overnight. The next day, the whole hair follicles were plucked and isolated from the skin by a pair of elaborate tweezers, treated with a solution obtained by mixing 0.25% trypsin-EDTA (Thermo Fisher Scientific) and 7 mg/ml of DNase I (Roche, Basel, Switzerland) at 4:1 together with Dulbecco's Phosphate Buffered Saline (DPBS), cultured at 37° C. for 5 minutes, and then treated with 10% fetal bovine serum (FBS) to suppress the activity of trypsin. Thereafter, the cell suspension was filtered through a 40-μm diameter perforated nylon mesh (BD Biosciences, San Jose, CA, USA), and cell viability was measured using a trypan blue reagent.

1-3. Culture and Differentiation of Hair Follicle Cells

The hair follicle cells isolated from the mouse dorsal skin were aliquoted at a density of $1.0 \times 10^6$ per well in a 6-well plate, and cultured under the conditions of 37° C. and 5% $CO_2$ using a DMEM/F12 (3:1) medium supplemented with 10% FBS, 20 µl/ml of a B27 supplement, 20 ng/ml of a basic fibroblast growth factor (bFGF), 10 ng/ml of a glial cell line-derived neurotrophic factor (GDNF), 75 ng/ml of GDNF family receptor α1 (GFRα1), and 1% penicillin/streptomycin.

In order to differentiate hair follicle cells into germline cells, the hair follicle cells were aliquoted at a density of $2.0 \times 10^5$ per well in a 24-well plate containing mitotically inactivated SIM mouse embryo-derived thioguanine- and auabain-resistant feeder cells. Each cell was maintained in a mouse serum-free medium (mSFM) supplemented with 10 ng/ml of a glial cell line-derived neurotrophic factor (GDNF), 75 ng/ml of GDNF family receptor α1 (GFRα1), and 1 ng/ml of a basic fibroblast growth factor (bFGF).

1-4. Histological Analysis and Immunostaining

For a histological analysis, the testicles and the skin were fixed with a Bouin's solution (Sigma-Aldrich, St. Louis, MO, USA). The fixed tissues were cut into a thickness of 4 µm. After the cut tissues were deparaffinized, hematoxylin-eosin (H&E) staining was performed. The stained sections were fixed, and then observed with a Nikon TE2000 microscope using NIS Elements imaging software (Nikon, Tokyo, Japan).

For immunostaining, the cells were fixed with 4% paraformaldehyde and treated with 0.1% Triton X-100 diluted with DPBS at room temperature for 10 minutes in order to increase cell membrane permeability, and then a blocking process of suppressing non-specific bonding was performed by treating a 5% (w/v) bovine serum albumin (BSA, Sigma-Aldrich) solution at room temperature for 30 minutes. Next, the slide was reacted at 4° C. overnight by diluting primary antibodies, that is, rat anti-CD34 (BD Biosciences, 553731), mouse anti-promyelocytic leukemia zinc finger (PLZF; zinc finger and BTB domain containing 16 [Zbtb16], EMD Millipore, OP128), rabbit anti-GFRα1 (Abcam, ab8026), mouse anti-CD9 (EMD Millipore, CBL162), goat anti-Ret (R&D Systems, AF482), rabbit anti-NCAM (EMD Millipore, AB5032), goat anti-Oct-4 (R&D Systems, AF1759), rabbit anti-DDX4 (Abcam, ab13840), rabbit anti-DAZL (Abgent, AF1303a), rabbit anti-SOX9 (Enogene, E18-6330), rabbit anti-CK15 (Abcam, ab52816), rabbit anti-CK19 (Abcam, ab15463), mouse anti-CD59 (Abcam, ab9183), mouse anti-Cx43 (EMD Millipore, MAB3067), rabbit anti-Nanog (Abcam, ab21603), mouse anti-CK14 (Abcam, ab7800), goat anti-c-kit (Santa Cruz Biotechnology), and mouse anti-Cdx2 with a 5% BSA solution at 1:200. Thereafter, the slide was reacted with secondary antibodies, that is, Alexa Fluor 568-conjugated goat anti-mouse IgG, Alexa Fluor 568-conjugated goat anti-rat IgG, Alexa Fluor 568-conjugated donkey anti-goat IgG, Alexa Fluor 594-conjugated goat anti-mouse IgG (Thermo Fisher Scientific) or Tetramethylrhodamine (TRITC)-conjugated goat anti-rabbit IgG (Jackson ImmunoResearch) (1:200) at room temperature for 1 hour. After cells were washed with DPBS, counterstaining was performed using a Vectashield medium diluted with 4',6-diamidino-2-phenylindole (DAPI, Vector Laboratories, Burlingame, CA), and the extent of protein expression was evaluated by observing stained cells by a Nikon TE2000 fluorescence microscope (Nikon, Chiyoda-ku, Tokyo, Japan). The relative percentage of protein expression was measured by counting at least 5 images containing 10 or more cells and quantifying the total number of DAPI-stained nuclei per image.

1-5. Microarray Analysis of Genes

RNA was isolated according to the manufacturer's instructions using TRIzol and the PureLink RNA mini kit (Thermo Fisher Scientific). Total RNA was purified and amplified using the Ambion Illumina RNA amplification kit (Ambion, Austin, USA) in order to produce biotinylated cRNA. In brief, 550 ng of the total RNA was reverse-transcribed into cDNA using a T7 oligo(dT) primer. Second strand cDNA was synthesized by T7 RNA polymerase, transcribed, and labeled with biotin-NTP. After purification, the cRNA was quantified using the ND-1000 spectrophotometer ((NanoDrop, Wilmington, USA). Labeled cRNA samples (750 ng) were respectively hybridized to a mouse WG6 expression v.4 bead array (Illumina, Inc., San Diego, USA) at 58° C. for 16 to 18 hours. Array signals were measured using Amersham fluorolink streptavidin-Cy3(GE Healthcare Life Sciences) by a method designated in the bead array manual. The array was scanned with an Illumina bead array reader according to the manufacturer's instructions.

The quality of hybridization and overall chip performance were monitored by visual inspection of both internal quality control checks and raw scanned data. Raw data was extracted using software provided by the manufacturer (Illumina GenomeStudio v2011.1 (Gene Expression Module v1.9.0)). Array probes were transformed to log scale and subjected to quantile normalization.

The statistical significance of expression data was measured using a LPE test, and the result thereof was shown as a mean fold change over control. The false discovery rate (FDR) was minimized by adjusting P values using a Benjamini-Hochberg algorithm. The DEG set was subjected to hierarchical cluster analysis using complete linkage and Euclidean distance as a measure of similarity. Gene-enrichment and functional annotation analysis were performed using DAVID (http://david.abcc.ncifcrfgov/home.jsp). Data analysis and visualization of all differentially expressed genes were performed using the R 3.0.2 program (www.r-project.org).

1-6. Methylation Analysis

The bisulfate treatment of DNA was performed using the EpiTect Bisulfite Kit (Qiagen, Spoorstraat, KJ Venlo, The Netherlands) according to the manufacturer's instructions. The bisulfate-converted DNA was amplified using a nested PCR approach. The primer sequences are shown in the following Table 1.

TABLE 1

| Gene[a] | | Forward primer (5'-3') | Reverse primer (5'-3') |
|---|---|---|---|
| H19 | outer | TAAGGAGATTATGTTT ATTTTTGGA | CCCCCTAATAACATTTATA ACCCC |
| | inner | AAGGAGATTATGTTTA TTTTTGGA | AAACTTAAATAACCCACAAC ATTACC |

TABLE 1-continued

| Gene[a] | | Forward primer (5'-3') | Reverse primer (5'-3') |
|---|---|---|---|
| Igf2 | outer | GGTTAGGTGAAGGTTTT GTGGGTAGTTATA | ATATTCCCCTTTCAAATTCC AATCTACATC |
| | inner | GGTGGTTTTTTAATGGA TATTTTAAGGTGA | CCAACCTCTATCCCTAACTT TTCTAACCTC |
| Peg1 | outer | AATTTGGGGTTTAGGAT TAGAGATTT | ACAACAAAAACAACAAACAA CAACT |
| | inner | AGAGATTTATAAGGAAA GAGGGGGTAG | ACAACAAAAACAACAAACAA CAACT |
| Peg3 | outer | TTTTGTAGAGGATTTTG ATAAGGAG | CATACTACAAAACAACCAAA TAACC |
| | inner | TGTAGAGGATTTTGATA AGGAGGTG | CAATCTAATACACCCACACT AAACC |

[a]H19 (H19, imprinted maternally expressed transcript), Igf2 (insulin-like growth factor 2), Peg1 (paternally expressed gene 1), Peg3 (paternally expressed gene 3)

The external primer pair was used for 1-round PCR, and the internal primer pair was used for 2-round PCR. The cycle parameters are as follows. 45 cycles of 95° C. for 10 seconds, 60° C. for 30 seconds, and 72° C. for 60 seconds; denaturation at 94° C.; and final elongation at 72° C. for 10 minutes. The amplification products were confirmed on 1% agarose gel by electrophoresis. Desired PCR products were subcloned into pGEM-T Easy vectors (Promega, Madison, WI), and sequenced using a T7 primer. Visualization and quantification of bisulfate-sequencing data were analyzed using the BiQ Analyzer software (Max Planck Society, Germany).

1-7. Karyotype Analysis

A colcemid (Thermo Fisher Scientific) solution was added to a cell culture solution, and cells were cultured at 37° C. under 5% CO2 for 1 hour. The cells were lysed in 0.25% trypsin and harvested in 15-ml tubes. The collected cells were treated with a hypotonic solution (75 mM KCl) at 37° C. for 25 minutes, and fixed with Carnoy's fixative (methanol:acetic acid=3:1) for 20 minutes. Metaphase chromosome spreads were prepared according to the standard procedure, and slides were Giemsa-stained for GTC banding. The results were analyzed using the ChIPS-Karyo Chromosome Image Processing System (GenDix, Inc. Seoul, Korea).

1-8. Transplantation

HF-derived germline stem cells (HFGSCs) and SSCs were collected, and each concentrated at a density of $50 \times 10^6$ cells/ml to $2.5 \times 10^6$ cells/ml. The mice to be subjected to transplantation were anesthetized with ketamine (75 mg/kg b.w.) and medetomidine (0.5 mg/kg, b.w.) through intraperitoneal injection. 80% of the seminiferous tubules were filled by microinjecting about 2 to 3 μL of a donor cell suspension into the seminiferous tubules of WBB6F1-W/Wv mice (6 to 12 weeks old) through an efferent duct.

1-9. Gamete Collection

Sperm was obtained from the seminiferous tubules of W/Wv mice 3 months after transplantation of HF-derived germline stem cells (HFGSCs). In order to produce metaphase II stage oocytes, the excessive ovulation of B6D2F1 (C57BL/6 female×DBA2 male F1 hybrid; Koatech) female mice was induced by intraperitoneally injecting 7.5 IU pregnant mare serum gonadotropin (PMSG; Sigma-Aldrich) and human chorionic gonadotropin (hCG) continuously at an interval of 48 hours, and cumulus-oocyte complexes were surgically isolated from the uterine tubes 13 to 14 hours after hCG injection.

Cumulus cells at the M2 stage were gently removed by 300 U/ml hyaluronidase, and oocytes were cultured in a potassium-modified simplex-optimized medium containing 0.4% BSA under 37° C. and 5% $CO_2$ conditions until the oocytes were used.

1-10. Intracytoplasmic Sperm Injection and Embryo Transfer

Intracytoplasmic sperm injection (ICSI) was performed in the metaphase II stage oocytes at room temperature using sperm, as previously known.

More specifically, adhesion was reduced by mixing a sperm solution with an M2 medium (Sigma-Aldrich) containing 10% (w/v) polyvinyl alcohol. Sperm heads were separated from their tails by mechanically applying various Piezo (Prime Tech) pulses, and loaded into an injection pipette (internal diameter, 7 mm). Subsequently, the zona pellucida was perforated using high Piezo pulses, and sperm heads were injected into the metaphase II cytoplasm using low Piezo pulses. Thereafter, after the resultant was cultured in the M2 medium for 15 minutes and recovered, ICSI-injected oocytes were cultured in KSOM-BSA under 37° C. and 5% $CO_2$ conditions.

It was determined that the ICSI-injected fertilized oocyte was normally changed into a second polar body and two pronuclei 6 hours after the injection. The 2-cell stage embryos were transferred into the hydrosalpinx of 0.5 day post coitum pseudopregnant ICR females, or the rates of blastocyst formation and apoptosis were analyzed by culturing the 2-cell stage embryos in KSOM-BSA for an additional 3 days.

1-11. TUNEL Assay

In order to detect apoptotic blastomeres in blastocysts, a terminal deoxynucleotidyl transferase-mediated dUTP-digoxigenin nick end-labeling (TUNEL, Roche, 12-156-792-910) analysis was performed using an in-situ cell apoptosis detection kit (Roche). The blastocysts were harvested on day 4, washed three times with DPBS-PVA, and fixed in 4% paraformaldehyde at 4° C. overnight. The fixed blastocysts were permeabilized with DPBS containing 0.5% (v/v) Triton X-100 at room temperature for 60 minutes. Non-specific binding sites were blocked by culture with PBS containing 10 mg/ml BSA at constant temperature for 1 hour. Thereafter, the blastocysts were washed three times with PBS-PVA, stained with TUNEL at 37° C. for 1 hour, and then washed three times with DPBS-PVA again, and placed on a glass slide along with DAPI. The number of total cells and the number of apoptotic cells per blastocyst were determined by counting the nuclei with blue (DAPI) and red (TUNEL) signals under a fluorescence microscope (Olympus).

1-12. Quantitative Real-Time Polymerase Chain Reaction (RT-PCR)

Total RNA was prepared from each sample with the PureLink RNA Mini Kit (Thermo Fisher Scientific) and reverse-transcribed using a superscript III reverse transcriptase (Thermo Fisher Scientific) according to the manufacturer's instructions. A quantitative real-time polymerase chain reaction (qRT-PCR) was performed using the SYBR green PCR Master Mix (Applied Biosystems) in a 7500 real-time PCR system (Applied Biosystems). All gene expression levels were measured by qRT-PCR and normalized to GAPDH levels, and real-time PCR primer sequences are as shown in the following Table 2.

TABLE 2

| Gene[a] | Forward primer (5'-3') | Reverse primer (5'-3') |
| --- | --- | --- |
| Bcl6b | CATTTTCGGCACAAGAGTCA | TTAGATGGTGGGGACTCAGC |
| Dnd1 | CCCTAAATGGGTTAAGCAGAGC | GGCAAGGTTCCTCACAACTAAAG |
| Egr3 | TTTGCCTGTGAGTTCTGTGG | CCCCTTTCTCCGACTTCTTC |
| Fos | TACACTCCAAGCGGAGACAG | TCCTTCTCCTTCAGCAGGTT |
| Id4 | GCTCGTGCCTACCATCCCGC | GGTGGCGGCTGTCTCAGCAAA |
| Nanos3 | CAAGCCAAGTTCAGAAAGCCAGCA | AGGACATGGGACTGATAGATGGCA |
| Ret | TCCCTTCCACATGGATTGA | ATCGGCTCTCGTGAGTGGTA |
| Sall4 | AGCACTGC TGCACACGGTGTG | GTCATGTAGTGTACCTTCAGG |
| Thy1 | TGGACTGCCGCCATGAGAATAACA | TGGTGGTGAAGTTGGCTAGGGTAA |
| Dazl | TCCTTGACTTGTGGTTGCTG | CCACCTTCGAGGTTTTACCA |
| Gapdh | CTGACGTGCCGCCTGGAGAAAC | CCCCGGCATCGAAGGTGGAAGAGT |

[a]Bcl6b (previously known as Bazf, B-cell CLL/lymphoma 6, member B (zinc finger protein)), Dnd1 (DND microRNA-mediated repression inhibitor 1), Egr3 (early growth response 3), Fos (FBJ osteosarcoma oncogene), Id4 (Inhibitor of DNA binding 4), Nanos3 (nanos homolog 3), Ret (ret proto-oncogene), Sall4 (sal-like protein 4), Thy1 (thymus cell antigen 1), Dazl (deleted in azoospermia-like), Gapdh (glyceraldehyde 3-phosphate dehydrogenase)

1-13. Genotyping

Genomic DNA identified from the tails of the offspring was PCR-amplified using primers (see Table 3). The PCR products were electrophoresed on agarose gel, and then stained with SYBR green (Thermo Fisher Scientific).

TABLE 3

| Gene[a] | Forward primer (5'-3') | Reverse primer (5'-3') |
| --- | --- | --- |
| Gfp | GCAAGCTGACCCTGAAGTTCA | TCACCTTGATGCCGTTCTTCT |
| Actb | CGCCATGGATGACGATATCG | CGAAGCCGGCTTTGCACATG |

[a]Gfp (green fluorescent protein), Actb (beta-actin)

1-14. Fluorescence-Activated Cell Sorting Analysis

Cultured hair follicle cells were stained with a rat anti-mouse CD34 antibody (BD Biosciences) on ice for 20 minutes. The cells were washed twice with PBS-S, and cultured along with an Alexa Fluor 568-conjugated anti-rat IgG (Thermo Fisher Scientific) secondary antibody on ice. The stained cells were washed twice with PBS-S, and re-suspended in PBS-S to which 1 µg/ml of propidium iodide (PI) was added. FACS analysis and cell alignment were performed using a BD FACSAria II flow cytometer (BD Biosciences, Research Facility Center, Chung-Ang University), and at least 10,000 pieces of data were obtained. Data analysis was performed using BD FACS Diva software.

1-15. Statistical Analysis

All statistical analyses were performed using GraphPad Prism (Version 5). The difference in colony formation and in vitro fertilization among the treatment groups were evaluated using a two-tailed Student's t-test, and $P<0.05$ was considered to be statistically significant. In this case, when the sizes of the groups were not the same, calibration (Welch's correction) was performed. Quantification of protein expression by cell population and treatment conditions was evaluated using a one-way variance analysis (ANOVA) and Tukey's post-hoc, and $P<0.05$ was considered to be statistically significant.

Example 2. Production of Hair Follicle-Derived Germline Stem Cells (HFGSCs)

Oct4 known as POU5F1 is a homeodomain transcription factor of the POU family. Oct4 is a protein of 352 amino acids belonging to the POU protein V class, and is encoded by the POU5F1 gene in humans. Oct4 is a pluripotency-associated gene, plays an important regulatory role in an early mammalian embryo, and is expressed in the inner cell clumps of unfertilized ova and primordial germ cells. In particular, Oct4 is a core transcription factor regulating pluripotency as well as self-renewal in embryonic stem cells. Nanog/Oct4 binding to low-methylated DNA serves to maintain the state of a pluripotent and undifferentiated cell. Further, cells are differentiated into the somatic lineage along other pathways without Oct4, whereas Oct4-expressing cells have the potential to develop into germ cells.

Thus, in order to evaluate effects of general germline stem cell (GSC) culture conditions on the transdifferentiation of hair follicle cells into germline cells, hair follicle cells were cultured under a GSC culture condition consisting of a mouse serum-free medium (mSFM) supplemented with GDNF, GFRα1, bFGF and inactivated STO feeder cells as described in Example 1-3, and after 3 to 5 weeks of culture, octamer-binding transcription factor 4 (Oct4)-GFP-expressing cells were observed by a fluorescence microscope.

Figure 2:
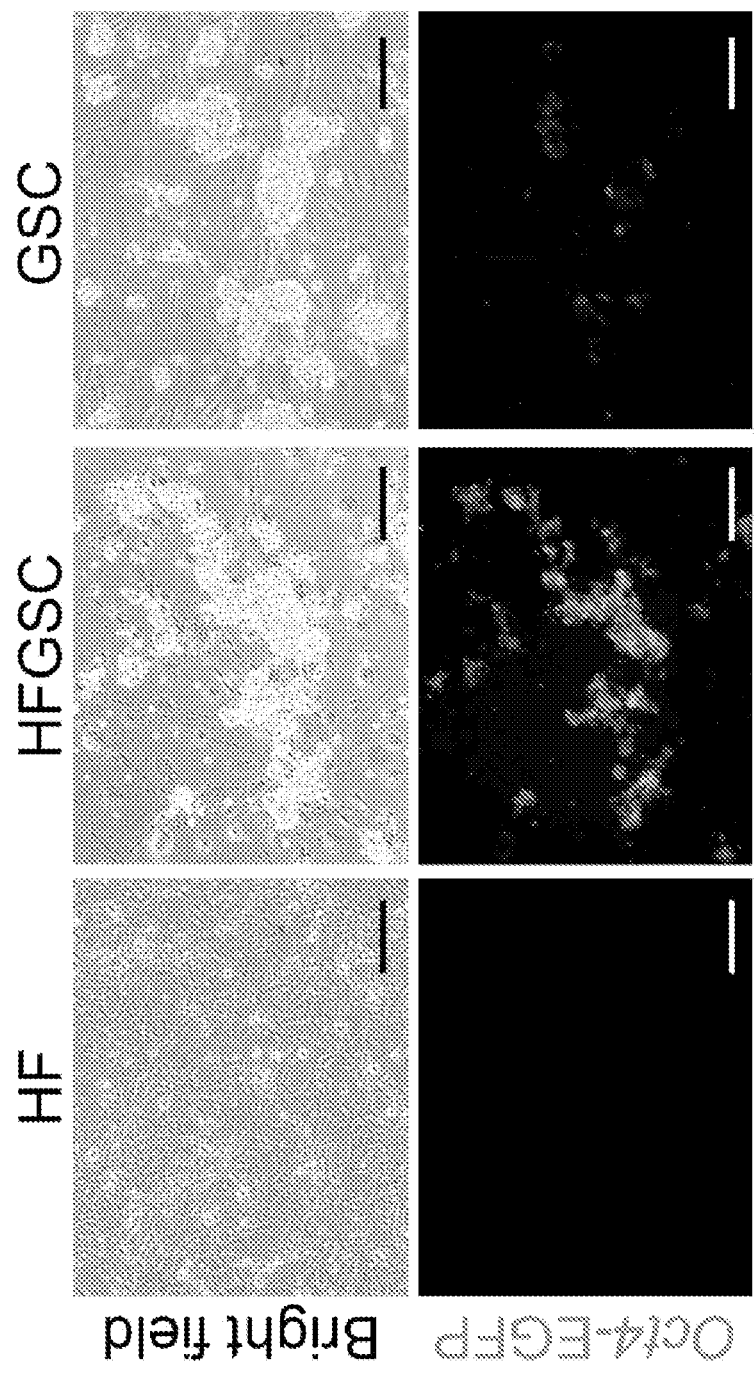
FIG. 2 is a view confirming results of culturing hair follicle (HF) cells, hair follicle-derived germline stem cells (HFGSCs) and germline stem cells (GSCs) under the GSC culture conditions without genetic modification.

As a result, as illustrated in FIG. 2, it could be confirmed that expanded colonies that were morphologically distinguishable from mouse GSCs were formed, and hair follicle-derived germline stem cell-like cells (HFGSCs), which exhibited strong EGFP expression, were greatly different from a basic fibroblast morphology of hair follicle cells, and were morphologically similar to GSCs, were observed.

In addition, in order to confirm that the proliferation (growth rate) of cultured cells is different from that of hair follicle cells, the growth rate of the germline stem cell-like cells was measured for 1 week.

Figure 3:
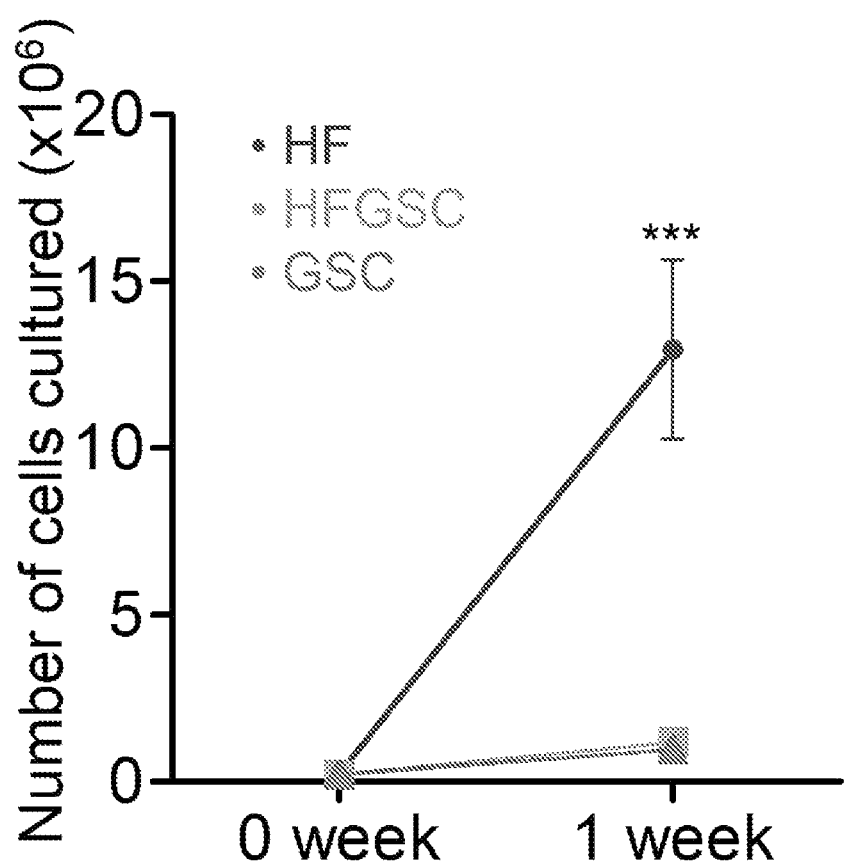
FIG. 3 is a view illustrating the growth rates of hair follicle (HF) cells, hair follicle-derived germline stem cells (HFGSCs) and germline stem cells (GSCs).

As a result, as illustrated in FIG. 3, it could be confirmed that hair follicle cells cultured in a serum-containing medium did not exhibit EGFP expression, exhibited a cardiac fibroblast morphology, and were proliferated at a rate which is 11 times or 14 times faster than that of HFGSCs or GSCs, respectively. The of HFGSC and GSC growth rates were shown to be similar to each other.

As a result of combining the aforementioned contents, it could be seen that when hair follicle cells were maintained under the GSC culture conditions, the morphology and growth rate of hair follicle cells were altered so as to reflect the characteristics of GSCs, meaning that hair follicle-derived germline stem cells (HFGSCs) were produced.

Example 3. Phenotype Characteristics of Hair Follicle-Derived Germline Stem Cells (HFGSCs)

In order to analyze the characteristics of hair follicle-derived germline stem cells (HFGSCs) transdifferentiated from hair follicle cells, the expression of specific proteins in the cells was confirmed in order to compare the phenotypes of hair follicle cells, HFGSCs and GSCs.

Figure 4:
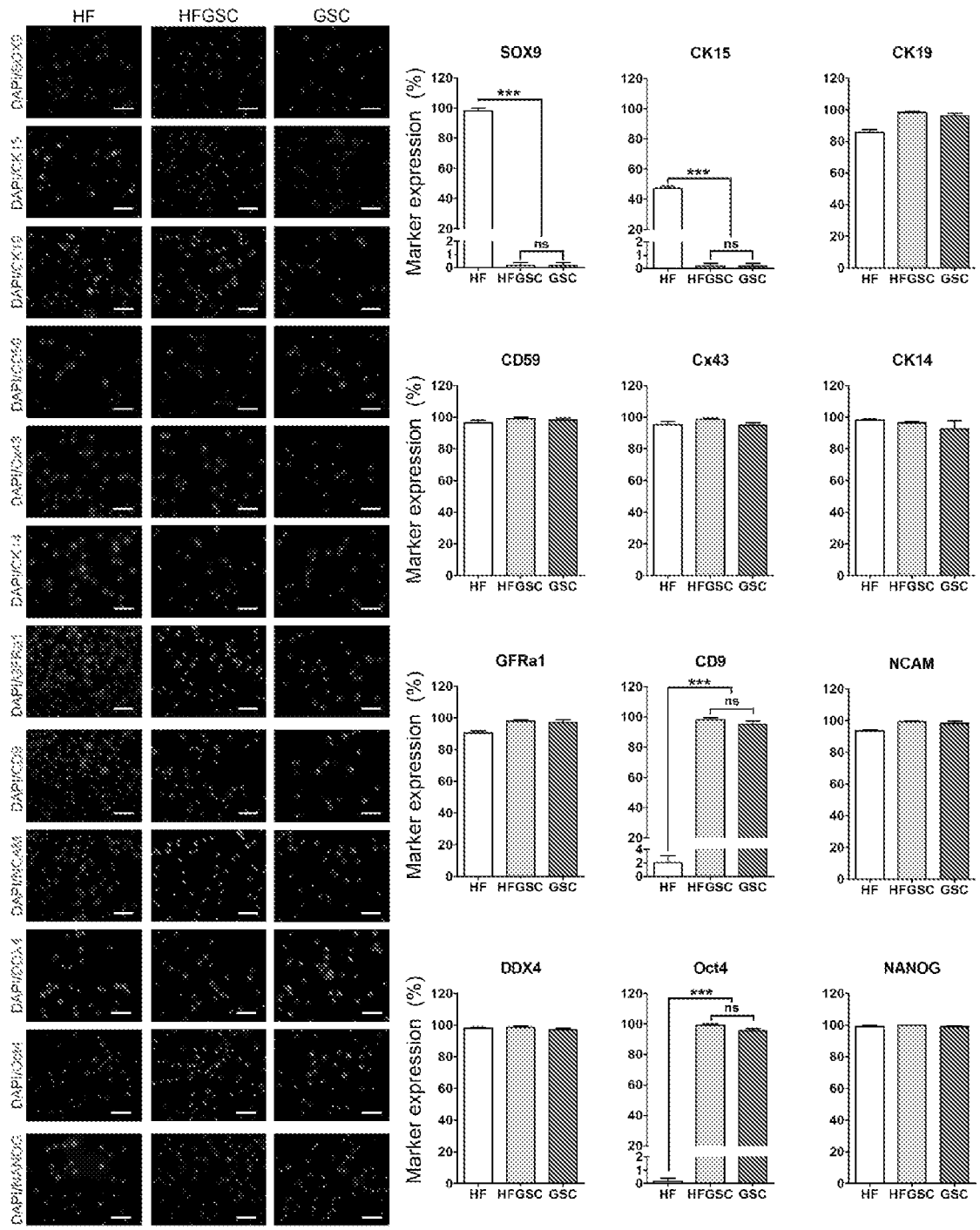
FIG. 4 is a view confirming whether specific markers for undifferentiated spermatogonia or hair follicle bulge cells are expressed through immunostaining of hair follicle (HF) cells, hair follicle-derived germline stem cells (HFGSCs) and germline stem cells (GSCs) and quantifying the number of cells expressing proteins.

As a result, as illustrated in FIG. 4, the expression of GFRα1, Ret, and NCAM which are markers for undifferentiated spermatogonia and DDX4 and DAZL which are markers for germ cells was confirmed in all three cell types of hair follicle cells, HFGSCs, and GSCs. Further, it was confirmed that a CD59 protein, which is a specific marker for hair follicle bulge cells, was also expressed in both HFGSCs and GSCs, but SOX9 and CK15, which are HF-stem cell markers, were expressed only in hair follicle cells.

Next, the expression of CD34, which is present in a small number of hair follicle cells, and thus is presumed to be a stem cell marker, and PLZF, which is a transcriptional repressor expressed by undifferentiated spermatogonia, was confirmed.

Figure 5:
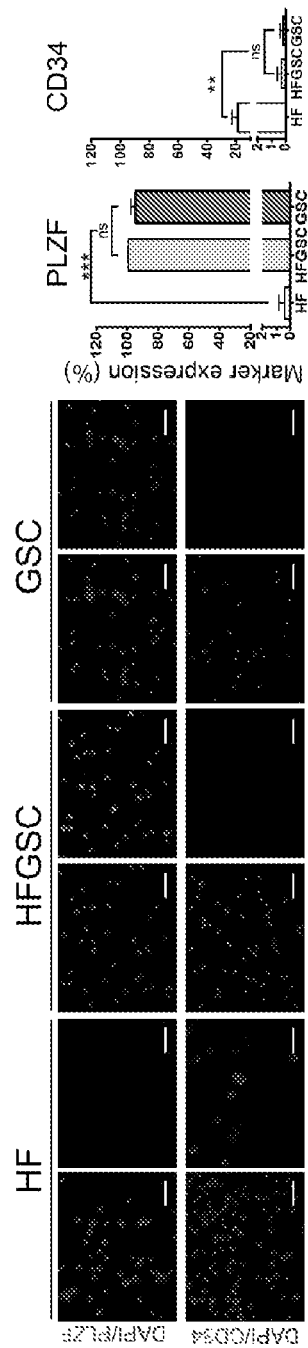
FIG. 5 is a view confirming whether the PLZF and CD34 of hair follicle (HF) cells and hair follicle-derived germline stem cells (HFGSCs) are expressed under the GSC culture conditions through immunofluorescence staining.

As a result, as illustrated in FIG. 5, hair follicle cells exhibited PLZF non-expression/CD34 expression, whereas HFGSCs and GSCs exhibited strong positive expression of PLZF, but CD34 was not expressed.

Further, after CD34-positive cells were isolated from cultured cells using fluorescence-activated cell sorting (FACS), the induction of HFGSCs was caused from each of CD34-positive and negative cells by spreading CD34-positive or negative cells again onto cell culture plates and changing the conditions into conditions corresponding to the GSC culture.

Figure 6:
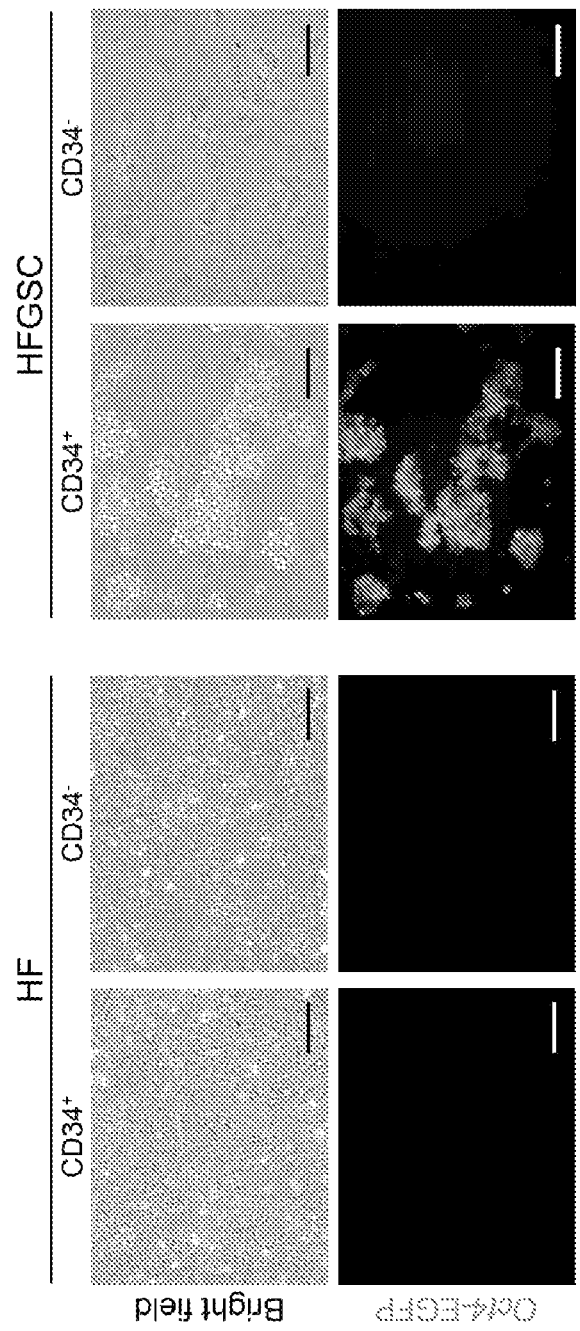
FIG. 6 is a view confirming the results of confirming CD34-positive/negative hair follicle cells and hair follicle-derived germline stem cells (HFGSCs) under the GSC culture conditions.

As a result, as illustrated in FIG. 6, Oct4-GFP-expressing HFGSCs were confirmed only in the CD34-positive group, and according to the morphological and immunofluorescence analysis of CD34-positive HFGSCs, these cells were confirmed to have a phenotype similar to those of HFGSCs and GSCs, and exhibited a GSC-like morphology such as the formation of clumps.

Through these results, it could be seen that as the culture conditions were varied without genetic modification, germline stem cells could be produced from hair follicle cells.

Example 4. Confirmation of Effects of Growth Factor on Proliferation of Hair Follicle-Derived Germline Stem Cells (HFGSCs)

A glial cell-derived neurotrophic factor (GDNF) is originally one type of the transforming growth factor beta (TGF-β) superfamily for stimulating the survival of midbrain dopaminergic neurons, but it has been revealed that GDNF regulates self-renewal of in vitro GSCs in the testicles and acts as an important growth factor for undifferentiated spermatogonia in vivo. In addition, it has been proved that GDNF activates an Src family kinase such as Src, Yes, Lyn, and Fyn by a RET-independent pathway, and the kinase plays an important role in self-renewal of GSCs. Furthermore, GDNF activates a phosphoinositide 3-kinase (PI3K)/Akt signal pathway which is a pathway associated with the GNDF-induced GSC self-renewal of in the GSC, and the PI3K/Akt signal pathway is specific for the GSC self-renewal and corresponds to an essential pathway for stimulating GSC survival, and the GDNF signal induces the activation of a Ras/ERK1/2 pathway in the GSC.

Thus, in order to confirm the effects of the growth factor on the proliferation of HFGSCs in vitro, parameters such as the formation, shape, and size of the colony were analyzed after HFGSCs were cultured with only GDNF and only bFGF or without any growth factor for 1 week by selectively treating the growth factor (the control (GDNF and bFGF) during the culture of HGGSCs.

Figure 7:
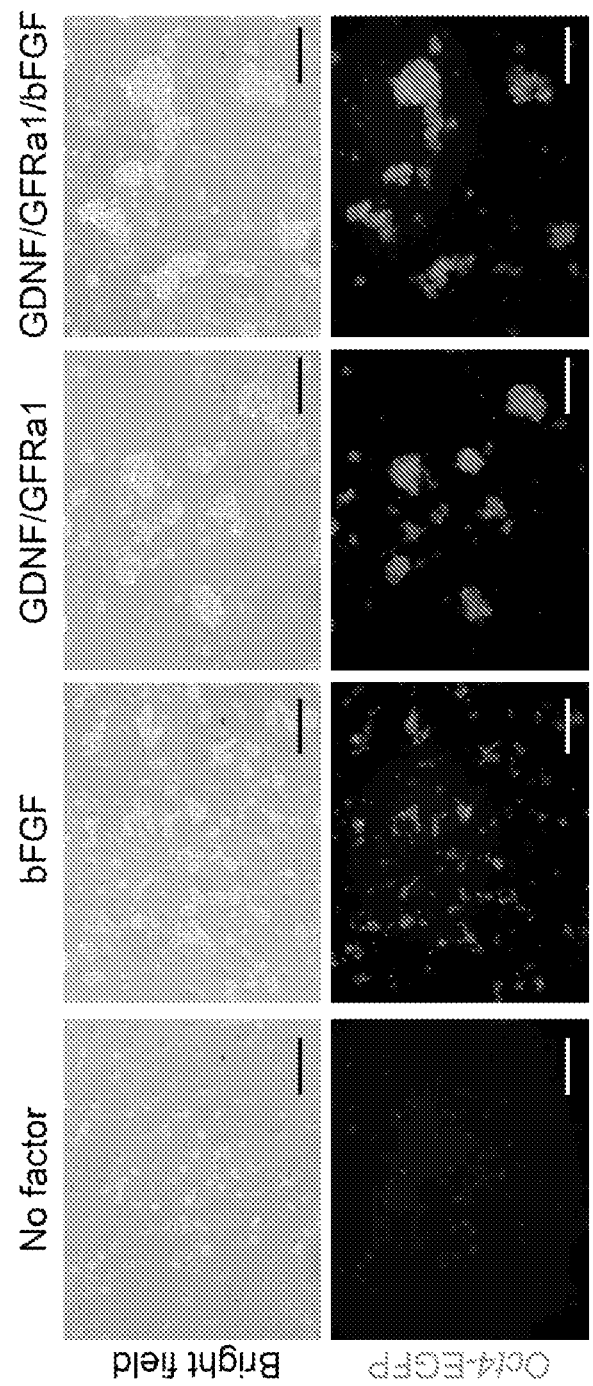
FIG. 7 is a view confirming the culture results under a condition in which a growth factor (GDNF and/or bFGF) is added/not added in order to confirm an effect of the growth factor on the proliferation of hair follicle-derived germline stem cells (HFGSCs).
Figure 8:
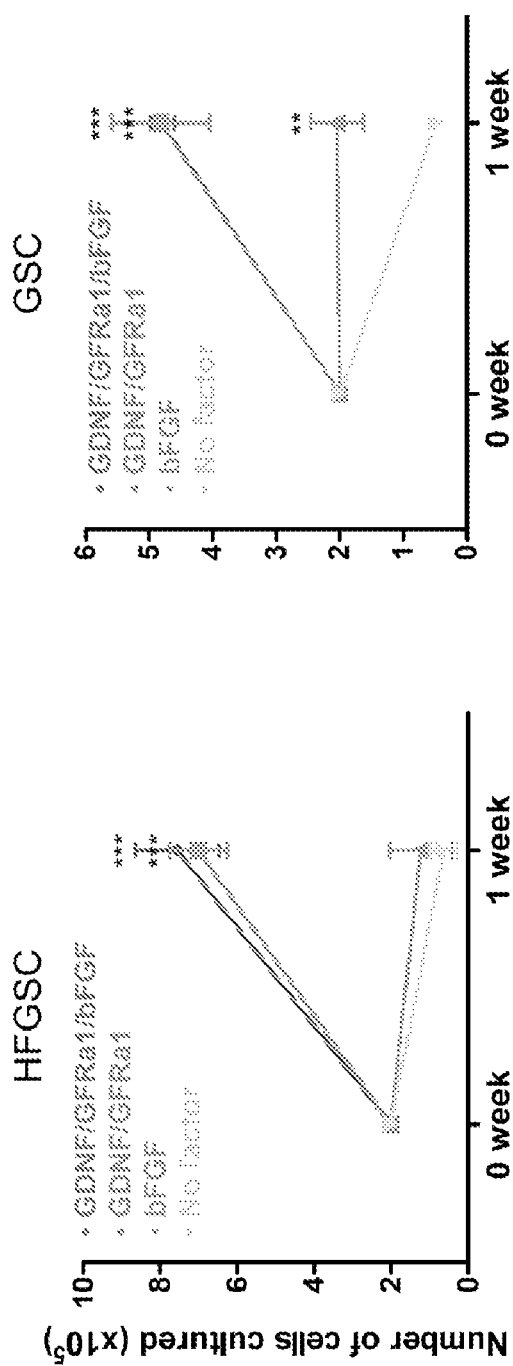
FIG. 8 is a view confirming the effects of the growth factors on the growth rates of hair follicle-derived germline stem cells (HFGSCs) and germline stem cells (GSCs).

As a result, as illustrated in FIGS. 7 and 8, the proliferation of cells in the group to which only bFGF was added was decreased by 6.3-fold ($7.6\times10^5 \pm 1.1$ v.s. $1.2\times10^5 \pm 0.8$) and a very small colony was formed, as compared to HFGSCs cultured in the medium containing both GDNF and bFGF. In addition, it was confirmed that when HFGSCs were cultured using GDNF alone or both GDNF and bFGF, the grow rate was 1.5 times higher than that of GSCs.

As a result of combining the aforementioned contents, it was shown that HFGSCs chemically depended on GDNF for normal growth under a serum-free condition (GSC condition), meaning that HFGSCs have phenotype characteristics similar to those of GSCs.

Example 5. Confirmation of Gene Expression Information on Hair Follicle-Derived Germline Stem Cells (HFGSCs)

In order to identify genetic information on hair follicle cells, HFGSCs, and GSCs, all cells were separately harvested and analyzed using an Illumina gene expression array, according to the method in Example 1-5, and accordingly, 45,281 genes were isolated, and 17,175 genes were confirmed.

Figure 9:
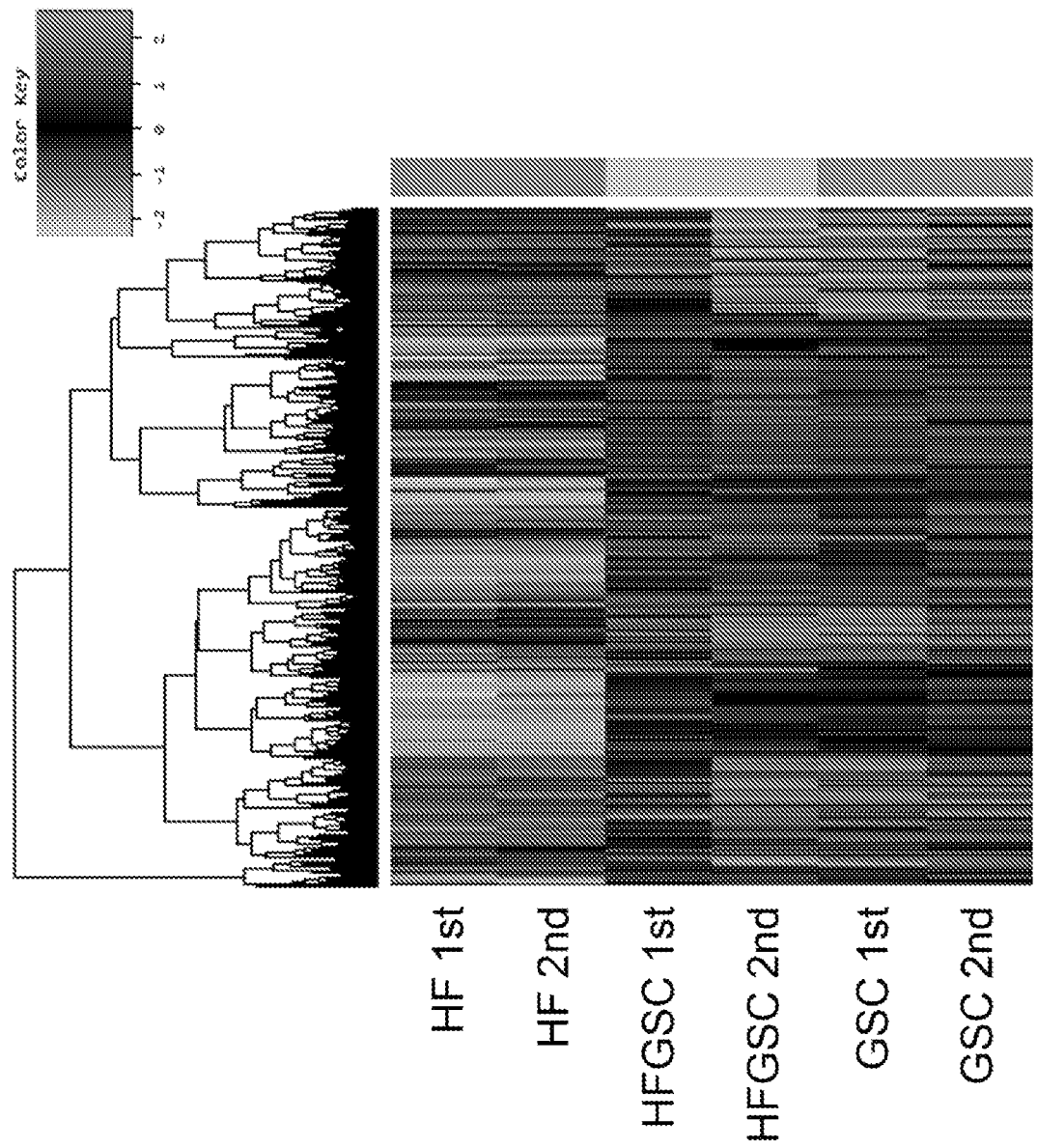
FIG. 9 is a view illustrating the global gene expression patterns of hair follicle (HF) cells, hair follicle-derived germline stem cells (HFGSCs) and germline stem cells (GSCs).
Figure 10:
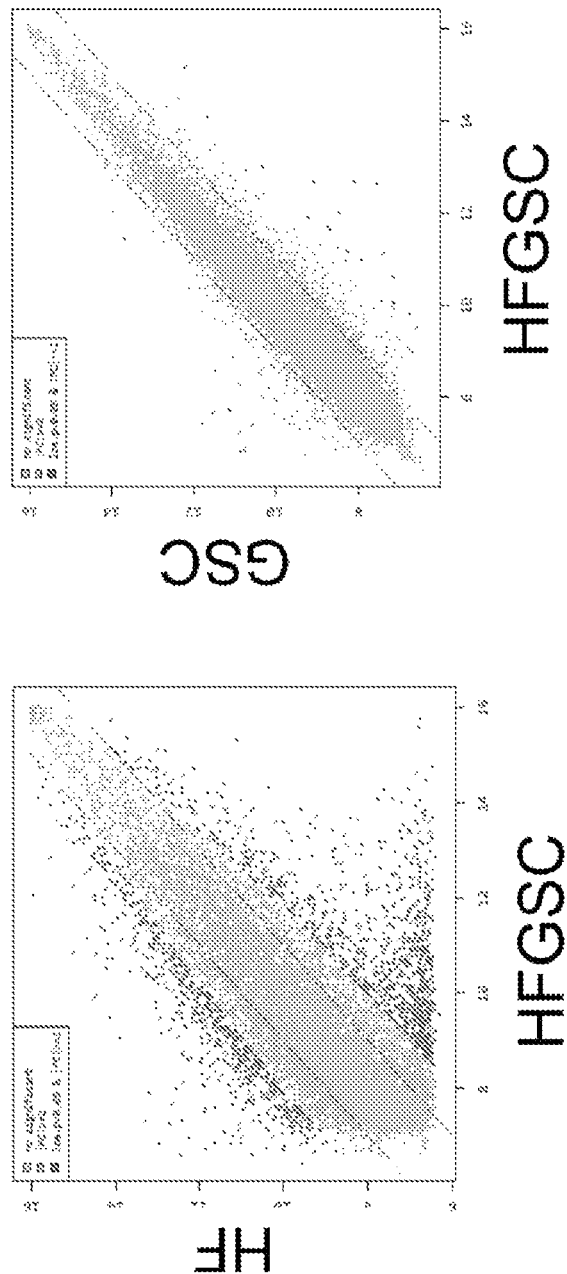
FIG. 10 is a view illustrating a pairwise scatter plot of hair follicle (HF) cells, hair follicle-derived germline stem cells (HFGSCs) and germline stem cells (GSCs) by a pairwise scatter plot for comparison of the global gene expression patterns.

As a result of a hierarchical cluster analysis, as illustrated in FIGS. 9 and 10, the gene expression information on HFGSCs was shown to be different from that of hair follicle cells with respect to expression pattern, but the similarity with GSCs was shown to be at a high level. Further, as shown in the following Table 4, it was shown that when hair follicle cells were cultured under GSC cell culture conditions, the expression of 1,702 genes was changed by at least 2-fold, and 2,784 genes are greatly different between GSCs and hair follicle cells. However, HFGSCs and GSCs were shown to be different only in the expression of 30 genes, meaning that HFGSCs have genetic characteristics similar to those of GSCs.

TABLE 4

| Gene expression | Number |
| --- | --- |
| Total processed genes | 45,281 |
| Total expressed genes by samples | 17,175 |
| Total genes regulated between HF and HFGSC 2-fold or greater | 1,702 |
| Total up-regulated between HF and HFGSC 2-fold or greater | 1,037 |
| Total down-regulated between HF and HFGSC 2-fold or greater | 665 |
| Total genes regulated between HF and GSC 2-fold or greater | 2,784 |
| Total up-regulated between HF and GSC 2-fold or greater | 1,460 |
| Total down-regulated between HF and GSC 2-fold or greater | 1,324 |
| Total genes regulated between HFGSC and GSC 2-fold or greater | 30 |
| Total up-regulated between HFGSC and GSC 2-fold or greater | 9 |
| Total down-regulated between HFGSC and GSC 2-fold or greater | 21 |

Figure 11:
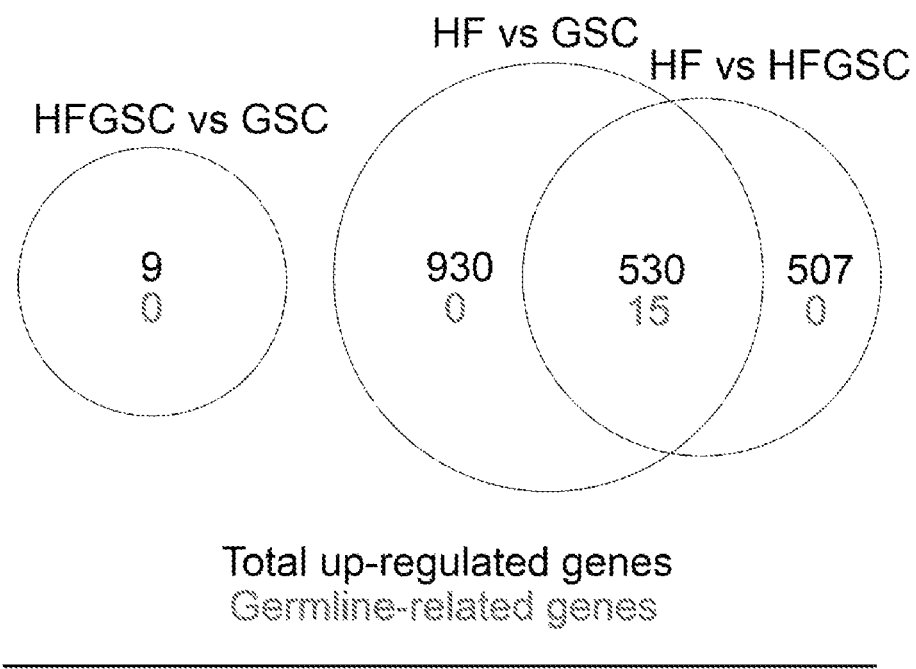
FIG. 11 is a Venn diagram illustrating the gene up/down-regulation which is important among hair follicle (HF) cells, hair follicle-derived germline stem cells (HFGSCs) and germline stem cells (GSCs).
Figure 11:
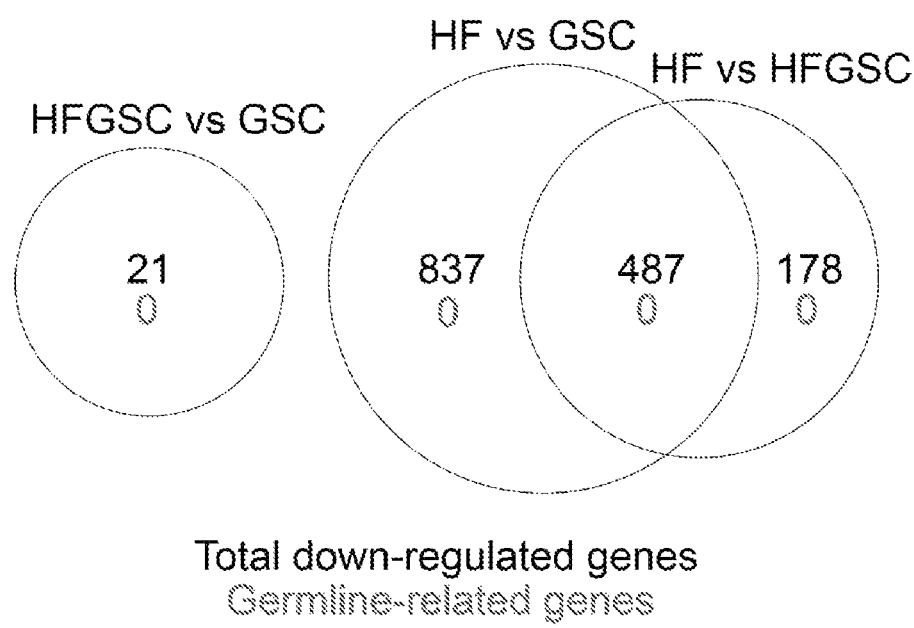
Figure 12:
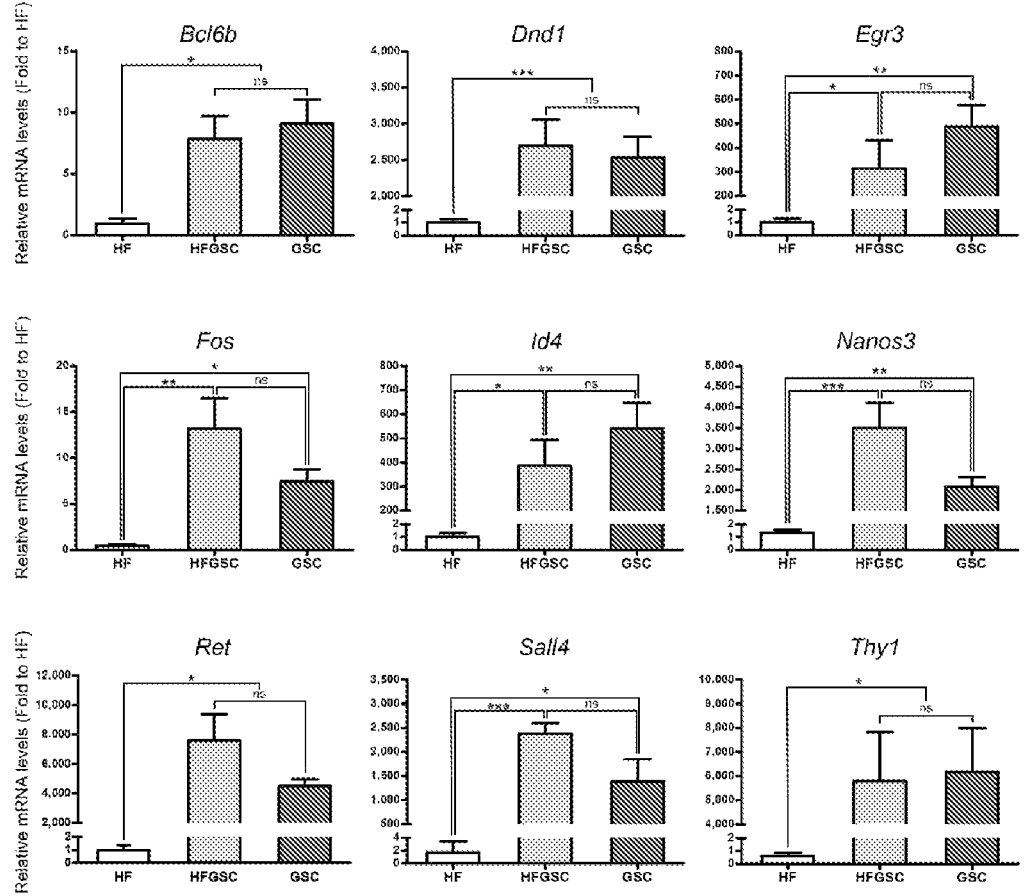
FIG. 12 is a view illustrating the qRT-PCR gene expression profiling results showing the difference in gene expression through a normalized fold-change due to the gene expression of hair follicle (HF) cells.
Figure 12:
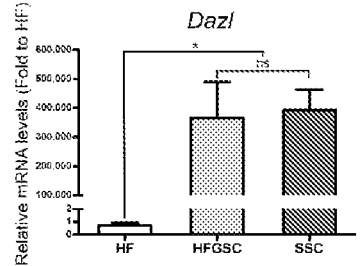

HF: Hair follicle cells;
HFGSC: Hair follide-derived germline stem cells;
GSC: Germline stem cells In addition, as a result of showing the analyzed genetic information using a Venn diagram in order to compare the inherent genetic information on hair follicle cells, HFGSCs, and GSCs, as illustrated in FIGS. 11 and 12, it was confirmed that HFGSCs expressed Bcl6b, Dnd1, Egr3, Etv5, Fos, Id4, Nanos3, Piwil2, Ret, Sall4, Thy1, and Zbtbl6 genes, which had been reported to be involved in the SSC self-renewal of mice in previous studies, at high levels, and it was confirmed that not only Sohlh1 and Kit, which are genes involved in the differentiation of SSCs, but also Dazl, which is a germ cell specific protein, were expressed.

Example 6. Genomic Imprinting and Karyotype Analysis of Hair Follicle-Derived Germline Stem Cells (HFGSCs)

In order to confirm the genomic imprinting pattern after the transdifferentiation of hair follicle cells, the methylation analysis in Example 1-6 was performed. The patterns of H19 and an insulin-like growth factor (Igf2), which are paternal genes of HFGSCs, and PEG1, Peg3, and Igf2r, which are maternal genes, were measured, and the patterns were compared with the methylation patterns of hair follicle cells and GSCs.

Figure 13:
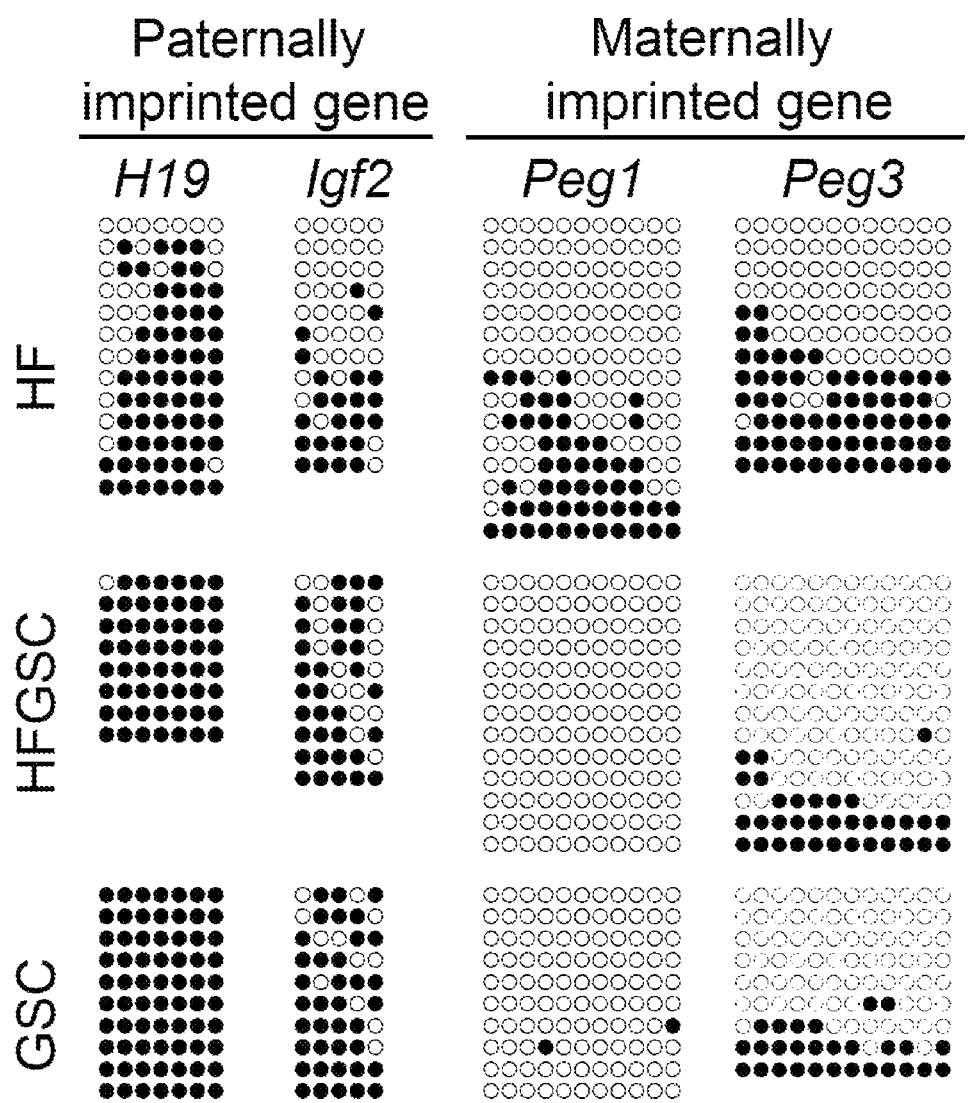
FIG. 13 is a view confirming the paternally or maternally imprinted gene region of hair follicle (HF) cells, hair follicle-derived germline stem cells (HFGSCs) and germline stem cells (GSCs) through differential methylation analysis.

As a result, as illustrated in FIG. 13, in the case of hair follicle cells, H19 and PEG1 were methylated, but Igf2 and Igf2r were not methylated, whereas in the case of HFGSCs, the methylation of PEG1 and Peg3, which are maternal imprinting genes, was decreased, but the methylation of H19 and Igf2, which are paternal imprinting genes, was increased, thereby exhibiting different methylation patterns in both paternal and maternal imprinting genes. In particular, in Igf2, the methylation pattern was greatly changed, so that the gene was completely methylated. Meanwhile, similar methylation patterns were observed between HFGSCs and GSCs. That is, for GSCs, H19 and Igf2, which are paternal imprinting genes, were also completely methylated, and PEG1, Peg3, and Igf2r, which are maternal imprinting genes, were not methylated. These results mean that during the transdifferentiation of HFGSCs from hair follicle cells, a change in imprinting pattern occurs.

Figure 14:
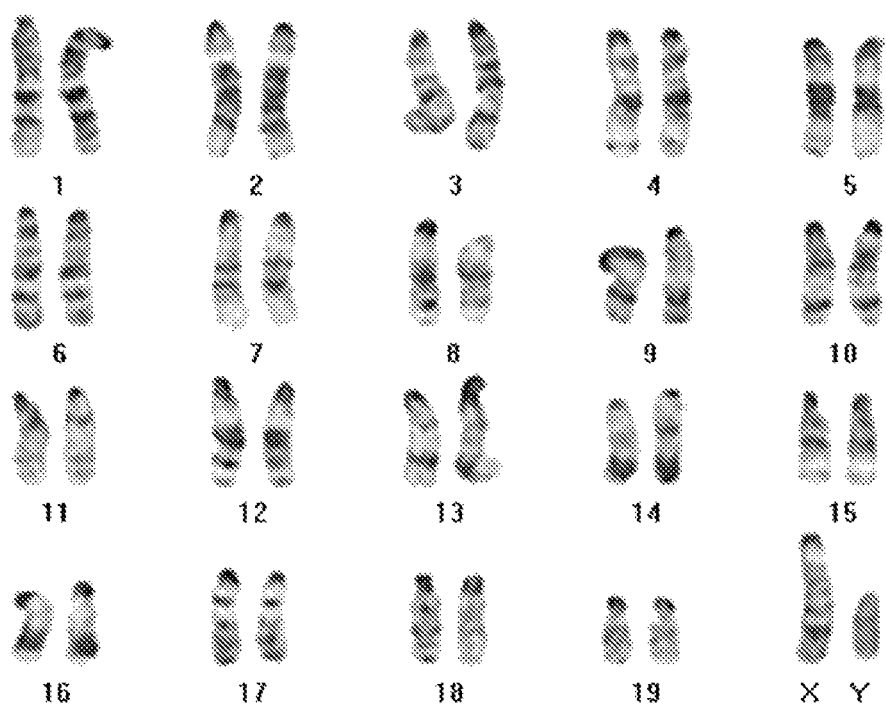
FIG. 14 is a view illustrating the karyotype analysis of hair follicle-derived germline stem cells (HFGSCs) cultured in vitro.

Further, in order to confirm the change in chromosomes of HFGSCs during the metaphase stage, as a result of performing a karyotype analysis according to the method in Example 1-7, as illustrated in FIG. 14, a normal diploid chromosome number (40, XY) was observed in 70% of all the analyzed cells.

As a result of combining the aforementioned contents, it was confirmed that the cultured HFGSCs were chromosomally stable, had a noticeable difference in imprinting pattern from hair follicle cells, and exhibited a change in genome imprinting similar to that of GSCs.

Example 7. Confirmation of Spermatogenesis of Hair Follicle-Derived Germline Stem Cells (HFGSC)

In order to evaluate the spermatogenic ability of donor-derived stem cells in the recipient testicles, cultured HFGSCs were transplanted through the seminiferous tubules of WBB6F1-W/W$^v$ mutant mice incapable of intrinsic spermatogenesis due to the lack of Kit signals, meaning that all the spermatogenesis of recipient WBB6F1-W/W$^v$ mutant mice entirely depends on donor stem cells after the transplantation. 2 to 3 months after the transplantation, the presence of Oct4-GFP-expressing donor-derived colonies was observed through a fluorescence microscope by sacrificing the recipient mice and isolating the testicles thereof.

Figure 15:
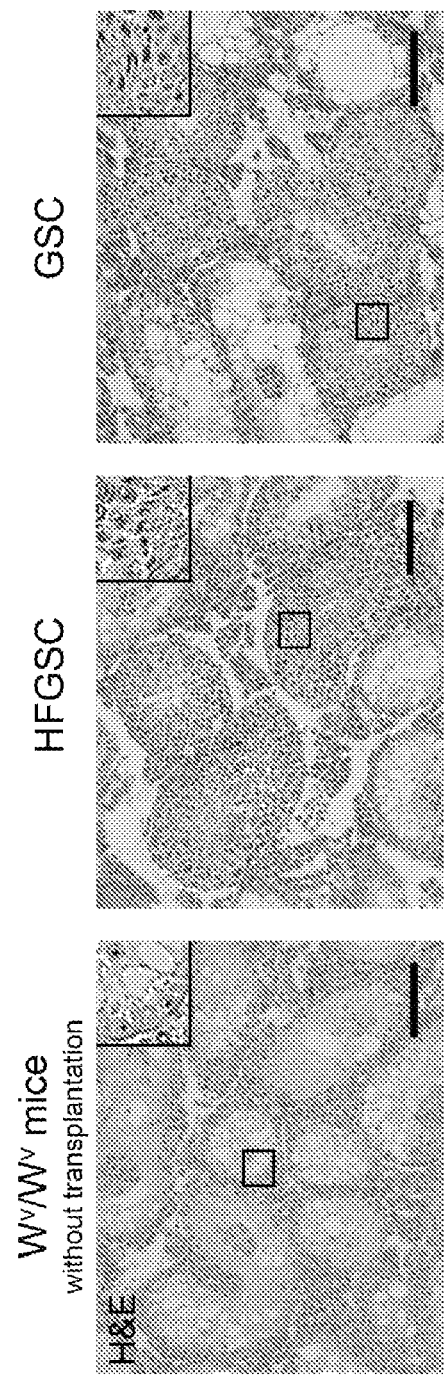
FIG. 15 is a view confirming the spermatogenesis in the testicles of WBB6F1-W/W$^v$ mutant mice through H&E staining.
Figure 16:
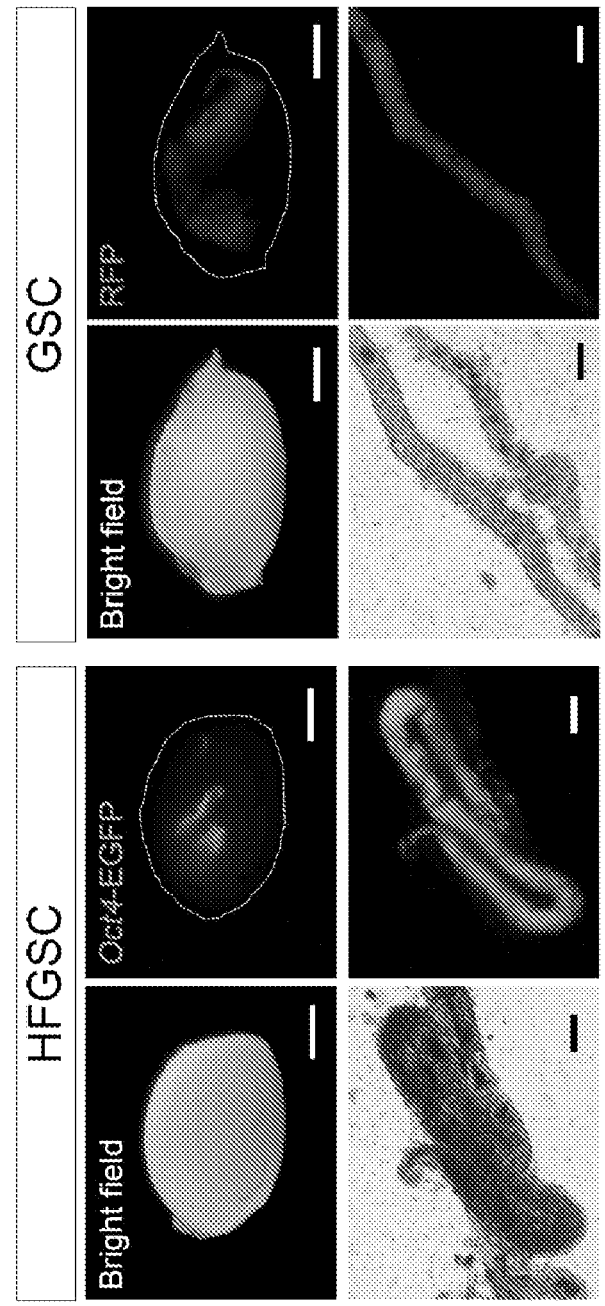
FIG. 16 is a view confirming the Oct4-GFP- or RFP-expressing colonies derived from donor HFGSCs in the seminiferous tubules of WBB6F1-W/W$^v$ mutant mice after the transplantation of hair follicle-derived germline stem cells (HFGSCs).
Figure 17:
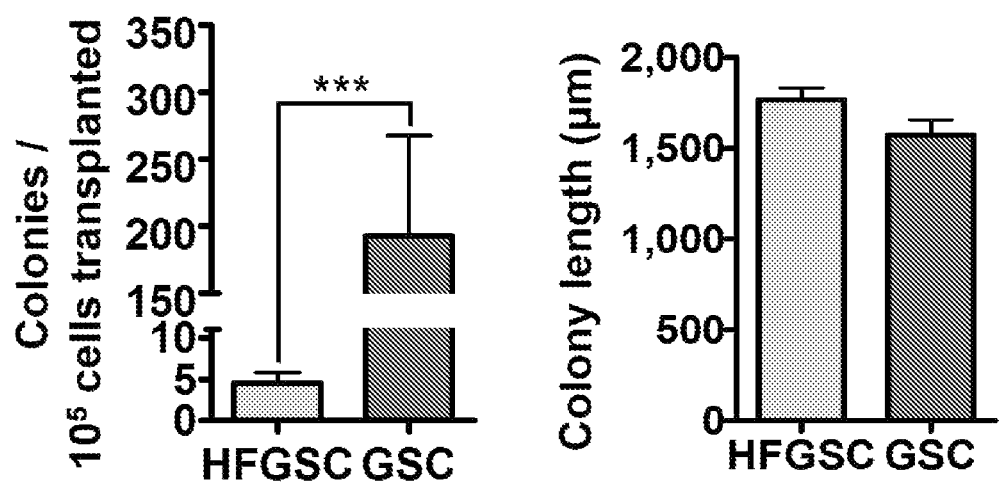
FIG. 17 is a view quantifying hair follicle-derived germline stem cells (HFGSCs) and germline stem cells (GSCs) based on the number of colonies expressing Oct4-GFP or RFP.
Figure 18:
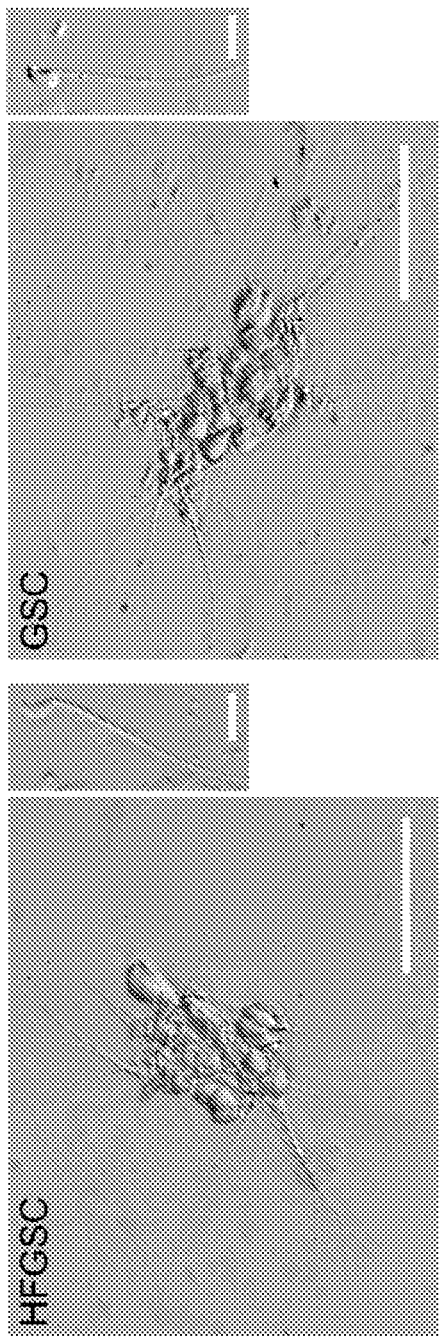
FIG. 18 is a view illustrating the spermatogenesis results induced from hair follicle-derived germline stem cells (HFGSCs).

As a result, as illustrated in FIG. 15, it was confirmed through a histological analysis that the spermatogenesis in the recipient testicles is similar to that of GSCs, whereas the spermatogenesis was not exhibited in the seminiferous tubules of WBB6F1-W/W$^v$ mice not subjected to transplantation. Further, as illustrated in FIG. 16, Oct4-GFP-expressing colonies derived from transplanted donor HFGSCs in the seminiferous tubules of WBB6F1-W/W$^v$ mice were confirmed, and as illustrated in FIG. 17, it was confirmed that the colony lengths (1768±62.7 μm v.s. 1574±84.4 μm, respectively, P>0.05) of HFGSCs and GSCs were similar, but the potential of HFGSCs to form colonies was remarkably lower than that of GSCs (192.3±75.2 colonies v.s. 4.5±1.3 colonies/100,000 transplanted cells). Finally, as illustrated in FIG. 18, the presence of Oct4-GFP-expressing cells was confirmed in elongated spermatids and sperm of the recipient mice.

Example 8. Confirmation of Fertility of Hair Follicle-Derived Germline Stem Cells (HFGSCs)

In order to confirm the fertility of recipient mice, spermatids of the HFGSC-derived colonies were collected and used in the intracelltoplasmic sperm injection (ICSI).

Figure 19:
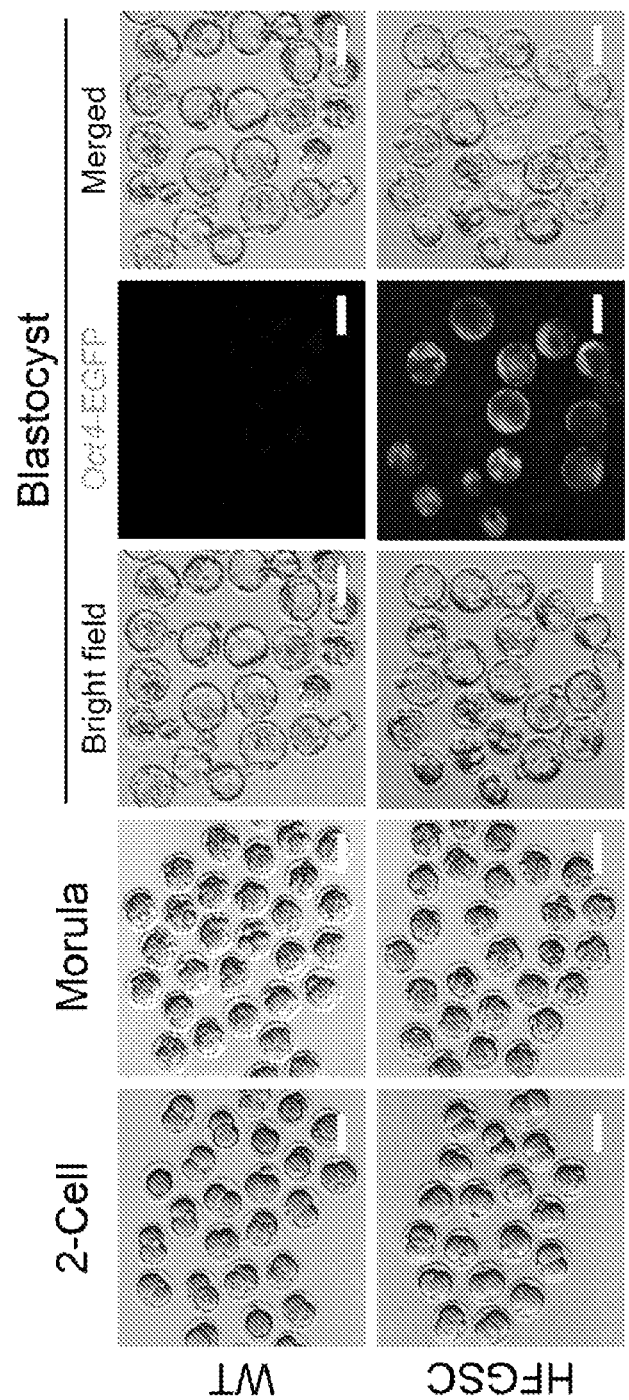
FIG. 19 is a view confirming the developmental process of oocytes fertilized with wild type (WT) or HFGSC-derived sperm step by step.

As a result, as illustrated in FIG. 19, EGFP expression was observed in HFGSC blastocysts carrying the Oct4-EGFP transgene similarly to the Oct-4 transcription activity of the developmental process.

Figure 20:
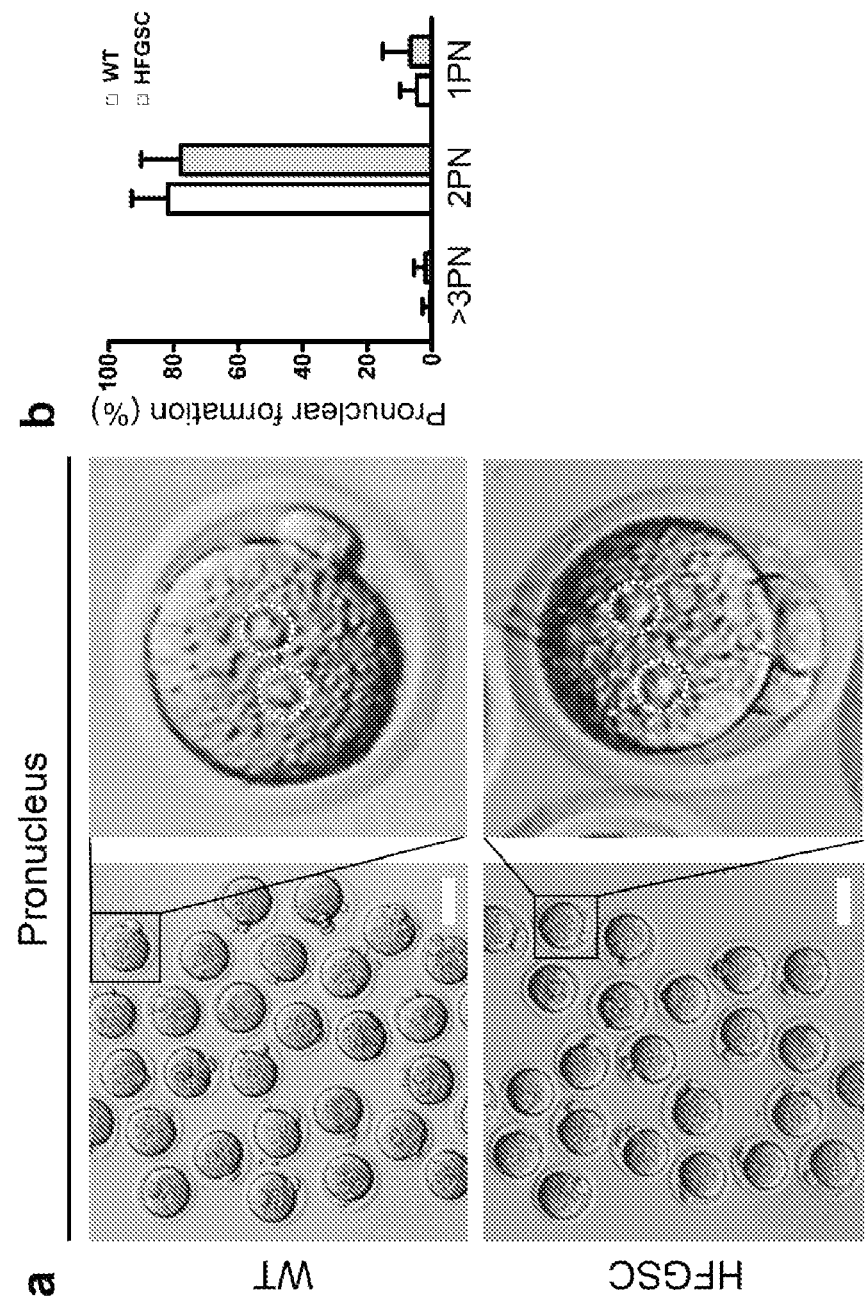
FIG. 20 confirms the pronuclear formation of putative zygotes into which the testicular spermatozoa of W/W$^v$ mice are ICSI-injected, and is a view illustrating (a) the shapes of pronuclei (yellow circles) at 7 to 8 hours after the ICSI and (b) the results of quantifying the survival rates, fertilization rates, and PN formation rates of wild type (WT) and W/W$^v$ testicular sperm.

In addition, as shown in FIG. 20 and the following Table 5, 187 (78%) of a total of 241 oocytes into which HFGSC-derived sperm had been injected were fertilized to form two pronuclear zygotes (2PN), of which 157 (84%) proceeded to the blastocyst stage in a normal form. In this case, no statistically significant difference was observed in the pronuclear formation frequency of the zygotes or the progression of embryos derived from WT or HFGSC sperm (that is, from the 2-cell stage to blastocyst stage).

TABLE 5

| Origin of spermatozoa | No. of oocyte inseminated | No. of oocytes forming pronucleus | No. of embryos developed to the following stages (%) | | | |
|---|---|---|---|---|---|---|
| | | | 2-cell | 4-cell | Morula | Blastocyst |
| WT | 247 | 202 | 199 (98.5 ± 2.6) | 188 (93.1 ± 4.3) | 177 (87.6 ± 6.3) | 170 (84.2 ± 6.2) |
| HFGSC | 241 | 187 | 182 (97.3 ± 2.8) | 176 (94.1 ± 5.3) | 168 (89.8 ± 8.2) | 157 (84.0 ± 11.6) |

Performed three times in total.

WT: Wild type, HFGSC: Hair follicle-derived germline stem cells.

Figure 21:
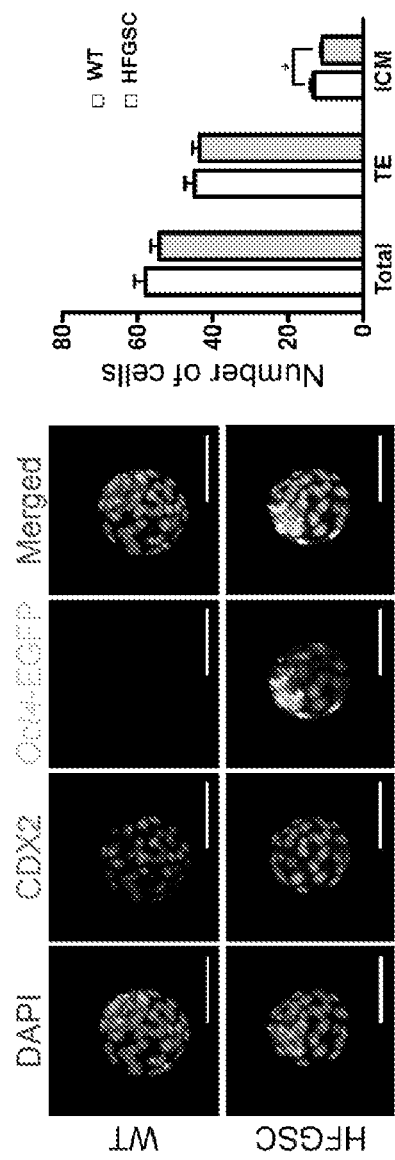
FIG. 21 is a view illustrating the results of quantifying the numbers of trophectoderm cells and ICM cells in the initial stage embryo using a CDX2 immunostaining method.
Figure 22:
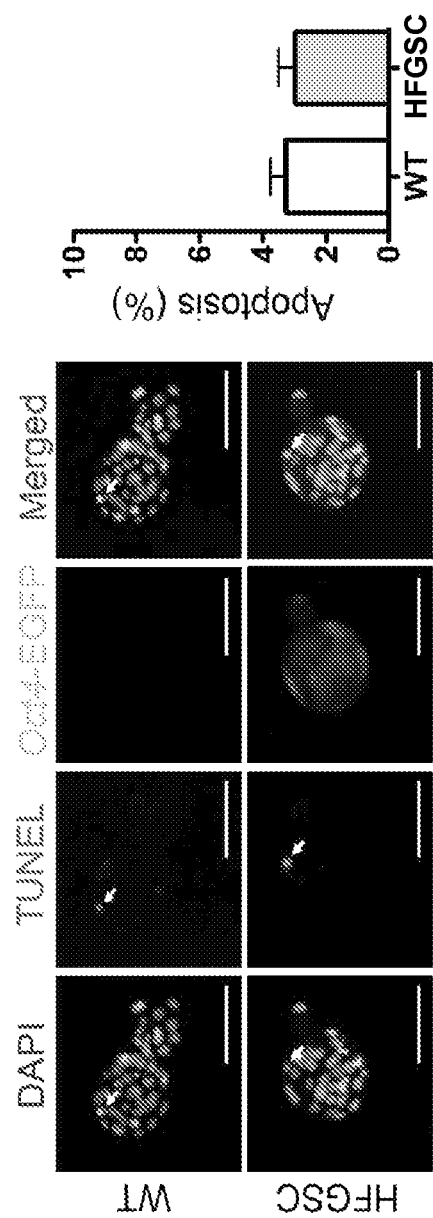
FIG. 22 is a view confirming the apoptosis of embryos derived from WT or HFGSC-derived sperm using a TUNEL analysis.

In addition, as illustrated in FIGS. 21 and 22, all WT and HFGSC-derived embryos exhibited strong expression of Cd×2, which is a transcription factor essential for the materialization of trophectoderm and developmental progression, and no significant difference was also observed in the number of total cells constituting the inner cell clumps or epidermal cells of WT or HFGSC-derived embryos. Furthermore, there is no difference in frequency of apoptosis occurring in WT or HFGSC-derived embryos.

Figure 23:
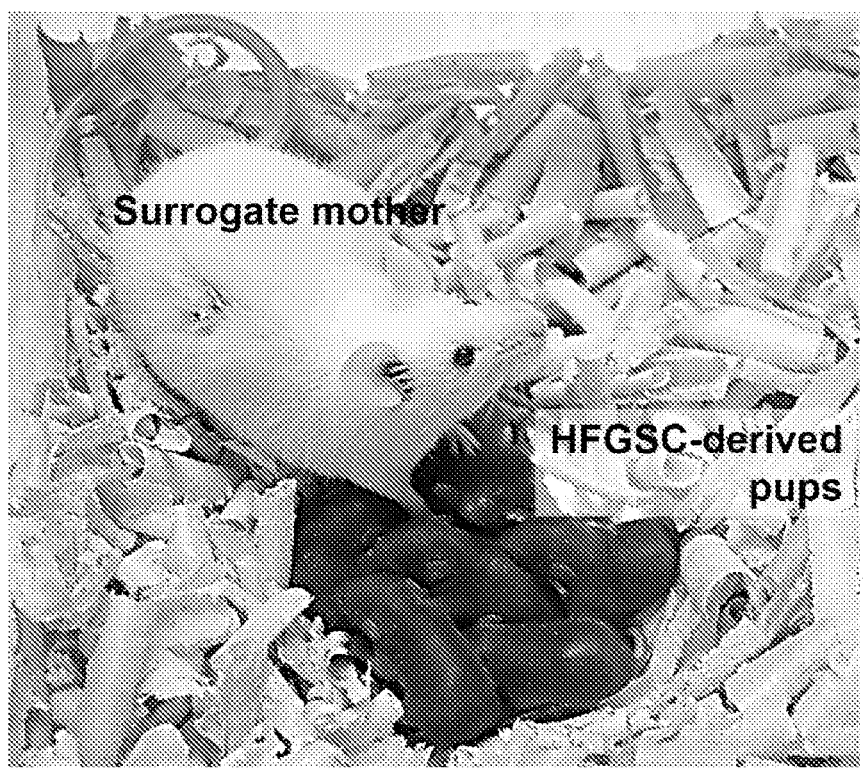
FIG. 23 is a view confirming descendants produced from HFGSC-derived sperm.
Figure 24:
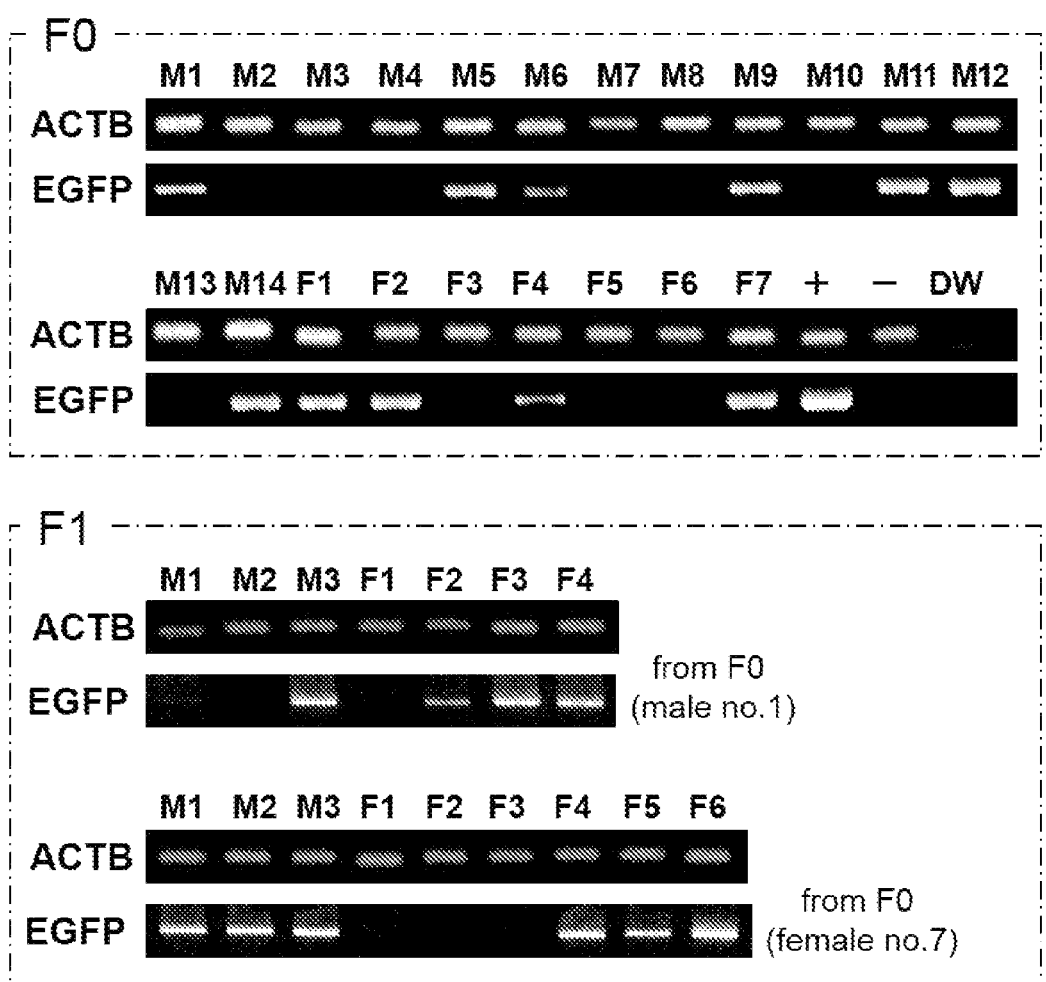
FIG. 24 is a view illustrating the PCR genotype analysis results of tail-tip DNA with respect to EGFP.
Figure 25:
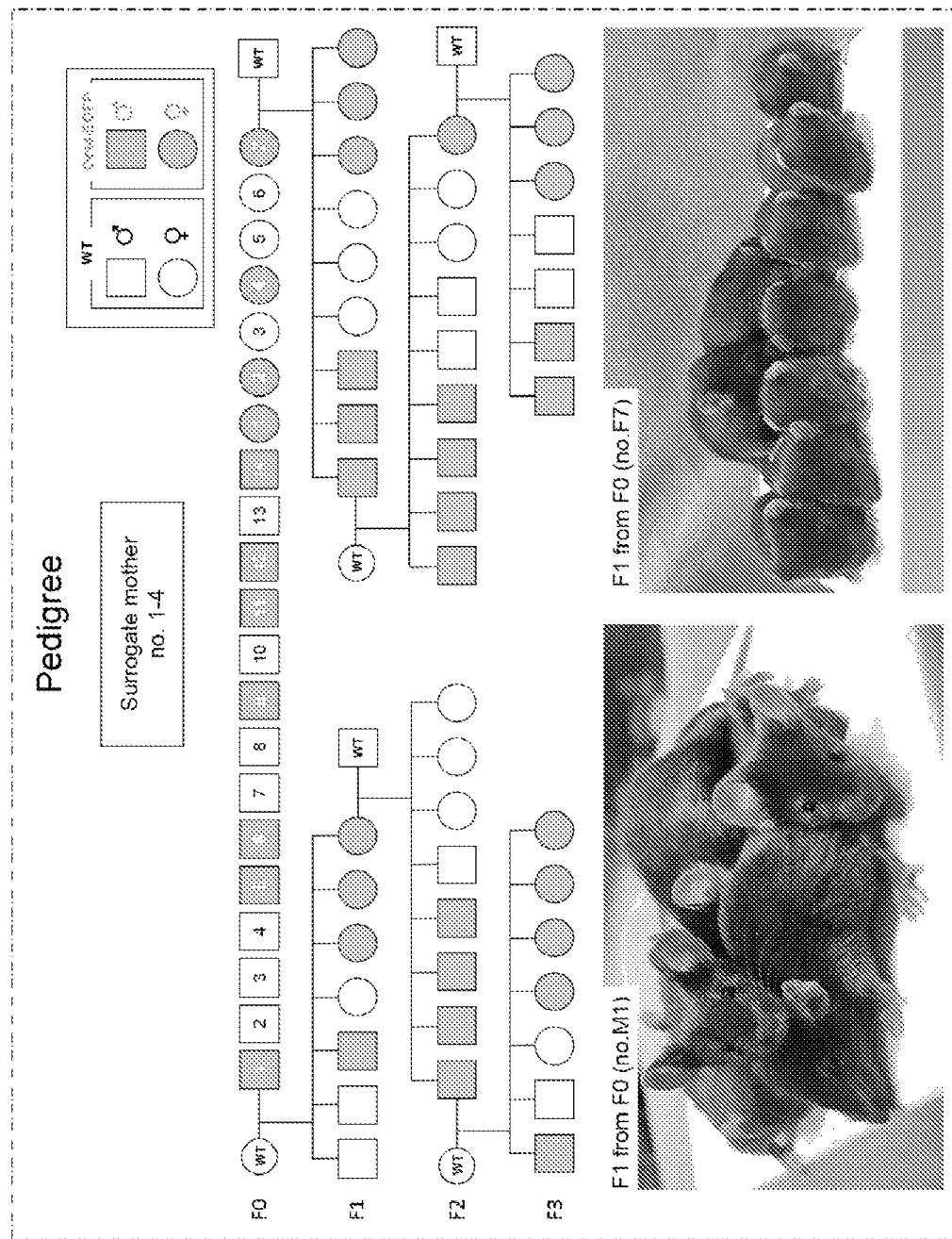
FIG. 25 is a view illustrating a pedigree map of F0 and F1 offspring.

Finally, offspring production efficiency was evaluated by implanting 82 HFGSC-derived zygotes into 4 female mice, and as a result, as illustrated in FIGS. 23 to 25, a total of 21 viable offspring was produced (FIG. 23). In this case, from PCR genotyping, the integration of the Oct4-EGFP transgene was confirmed in 11 of the 21 offspring (FIGS. 24 and 25), the fertility of these F0 males and females was confirmed from the birth of 16 F1 offspring, and it was confirmed that among them, 10 offspring had the transgenic EGFP gene (Table 6).

TABLE 6

| Origin of spermatozoa | No. of oocyte inseminated | No. of oocytes forming pronucleus | No. of 2-Cell embryos | No. of embryos transferred | No. of recipients | No. of live pups (male/female) |
|---|---|---|---|---|---|---|
| HFGSC | 104 | 84 | 82 | 82 | 4 | 21 (14 17) |

Performed twice in total.

HFGSC: Hair follicle-derived germline stem cells.

As a result of combining the aforementioned contents, it was confirmed that CD34$^+$ hair follicle cells cultured under the in vitro conditions of the present invention could acquire GSC-like characteristics while requiring no modification of exogenous genes. Furthermore, the ability of HFGSCs to be differentiated into functional sperm and produce viable offspring was confirmed, which is expected to be able to restore spermatogenesis and restore male fertility by providing a powerful approach to reproductive technology.

The above-described description of the present invention is provided for illustrative purposes, and those skilled in the art to which the present invention pertains will understand that the present invention can be easily modified into other specific forms without changing the technical spirit or essential features of the present invention. Therefore, it should be understood that the above-described Examples are illustrative only in all aspects and are not restrictive.

INDUSTRIAL APPLICABILITY

The present invention relates to a method for differentiating hair follicle cells into germline stem cells, germline stem cells differentiated by the method, and use of the same germline stem cells, and since it is possible to induce differentiation of cells of specific individual types, such as hair follicle cells, into cells of different types such as germline cells without genetic modification according to the present invention, the present invention is expected to be usefully used for the understanding of reproductive biology and the clinical application thereof.

The invention claimed is:

1. A method for transdifferentiating mouse hair follicle cells into sperm stem cells, the method comprising:
   a) isolating mouse hair follicle stem cells from the skin of a mouse; and
   b) culturing the isolated hair follicle stem cells in a medium comprising glial cell line-derived neurotrophic factor (GDNF), GDNF family receptor α1 (GFRα1), basic fibroblast growth factor (bFGF), and feeder cells such that sperm stem cells that express CK19, CD59, CX43, CK14, GFRa1, CD9, NCAM, DDX4, OCT4, NANOG, and DAZL capable of differentiating into sperm and producing offspring upon being injected into the testes of a mouse are obtained.

2. The method of claim 1, wherein the medium is mouse serum-free medium.

3. The method of claim 1, wherein the feeder cells are STO cells.

4. The method of claim 1, wherein the hair follicle stem cells are cultured for 3 to 5 weeks.

5. The method of claim 1, wherein the feeder cells secrete a wingless-type MMTV integration site family (Wnt), bone morphogenetic proteins (BMPs), a transforming growth factor-beta (TGF-β), or an extracellular matrix.

* * * * *